(12) United States Patent
Kim et al.

(10) Patent No.: US 7,245,365 B2
(45) Date of Patent: Jul. 17, 2007

(54) APPARATUS AND METHOD FOR DETECTING PARTICLES ON AN OBJECT

(75) Inventors: Deok-Yong Kim, Gyeonggi-do (KR); Duck-Sun Yang, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 316 days.

(21) Appl. No.: 10/822,055

(22) Filed: Apr. 8, 2004

(65) Prior Publication Data

US 2004/0201841 A1    Oct. 14, 2004

(30) Foreign Application Priority Data

Apr. 9, 2003   (KR)  .................... 10-2003-0022225

(51) Int. Cl.
*G01N 21/00* (2006.01)
(52) U.S. Cl. ............................... 356/237.2; 356/237.3; 356/237.4
(58) Field of Classification Search ..................... None
See application file for complete search history.

(56) References Cited

U.S. PATENT DOCUMENTS 4,740,079 A * 4/1988 Koizumi et al. ......... 356/237.4
5,225,886 A * 7/1993 Koizumi et al. ......... 356/237.4
5,317,380 A * 5/1994 Allemand ................... 356/338
6,144,446 A * 11/2000 Nagasaki et al. ........ 356/237.3
6,288,780 B1 * 9/2001 Fairley et al. ........... 356/237.1
6,313,913 B1 * 11/2001 Nakagawa et al. ...... 356/237.2

FOREIGN PATENT DOCUMENTS

| JP | 61-169750 | 7/1986 |
| JP | 11-284038 | 10/1999 |
| KR | 2000-0000242 | 1/2000 |
| KR | 2001-0086099 | 9/2001 |

OTHER PUBLICATIONS

English Language Abstract of Korean Publication No. 2001-0086099.

* cited by examiner

*Primary Examiner*—Michael P. Stafira
(74) *Attorney, Agent, or Firm*—Marger Johnson & McCollom, P.C.

(57) ABSTRACT

An apparatus for detecting particles located on an object includes an emitter for irradiating lights to the particles. The object is disposed on a stage in a direction substantially parallel to a surface of the object. The apparatus further includes a driver for generating a relative motion between the emitter and the object for scanning the surface of the object with the lights and a detector for detecting the lights emitted from the emitter or lights scattered from the particle. With embodiments of the present invention, the particles can be quickly detected.

38 Claims, 21 Drawing Sheets

APPARATUS AND METHOD FOR DETECTING PARTICLES ON AN OBJECT

CROSS REFERENCE TO RELATED APPLICATION

This application claims priority under 35 USC § 119 to Korean Patent Application No. 2003-22225 filed on Apr. 9, 2003, the contents of which are herein incorporated by reference in their entirety for all purposes.

BACKGROUND OF THE INVENTION

1. Field of the Invention

The present invention relates to an apparatus and a method for detecting particles on an object. More particularly, the present invention relates to an apparatus and a method for detecting particles on an object such as a wafer by irradiating a light to the particles.

2. Description of the Related Art

Generally, as the dimensions of a semiconductor device has been reduced, and the degree of integration of the semiconductor device has been augmented, it has required that the detection level for monitoring particles be improved. Since a cell size of the semiconductor device has been reduced, and also the size of the particles having an adverse influence on the electrical characteristics of the semiconductor are small, an apparatus capable of detecting a particle having a size of below about 0.1 μm has been developed and is used currently. The apparatus generally detects these particles using laser scattering techniques.

There is an issue concerning an ability of an apparatus in particle monitoring to distinguish the particle on a wafer from a critical oriented particle (COP). The COP serves as an initial defect caused by abnormality of crystalline structure of the wafer that is formed on the wafer in a V shape.

It is rare that the COP occurs on an initial-fabricated wafer. Accordingly, distinguishing the actual particle on the wafer from the COP in the initial-fabricated wafer is carried out without a problem. The wafers are, however, recycled due to high cost of using the wafer only once. When the used wafer is recycled, the COP level on the used wafer increases. The COP is readily distinguished from the actual particle on a bare wafer. However, when an oxide layer or a nitride layer is formed on the bare wafer, the COP is not readily distinguished from an actual particle on the bare wafer.

A conventional method for inspecting on a wafer is disclosed in Korean Laid Open Patent Publication No. 2001-0086099. In the conventional method, a light is reflected or scattered from a surface of a wafer. Light-receiving units receive the reflective or scattered light. A shape and a category of defects on the wafer are inspected according to ratio of light-receiving intensity in the light-receiving units.

FIG. 1 is a cross sectional view illustrating a conventional apparatus for detecting particles on a wafer.

With reference to FIG. 1, a conventional apparatus has two emitters and two detectors. The emitters include a first emitting member 10 for irradiating a first light having an incident angle of about 70° to a wafer W and a second emitting member 12 for irradiating a second light having an incident angle of about 9° to the wafer W. The detectors include a first detecting member 14 for detecting a first scattered light having a wavelength in a wide band reflected from the wafer W and a second detecting member 16 for detecting a second scattered light having a wavelength in a narrow band reflected from the wafer W. When the wafer W is a bare wafer. The COP has a shape different from that of the actual particle on the bare wafer. Thus, a signal detected in the detectors 14 and 16, which corresponds to the lights reflected from the COP, may be distinguished from a signal detected in the detectors 14 and 16, which corresponds to the lights reflected from the actual particle on the wafer W. Namely, the actual particle on the wafer and the COP may be distinguished using the difference between the respective signals.

FIG. 2A is a graph illustrating a ratio of a light having a wavelength in a narrow band relative to a light having a wavelength in a wide band of the light. With reference to FIG. 2A, the COP and the actual particle on the wafer are distinctly distinguished on the basis of a slope line having a ratio of about 1.5. The ratio corresponds to a ratio of the light having a wavelength in a narrow band detected by the second detecting member 16 relative to the light having a wavelength in a wide band detected by the first detecting member 14. Accordingly, when the bare wafer is monitored through irradiation of the lights from the first and second emitting members 10 and 12, the COP and the actual particle may be accordingly distinguished.

It is, however, that after an oxide layer or a nitride layer is formed on the bare wafer, the COP may be difficult to distinguish from the actual particle because the COP has a shape similar to that of the actual particle. Thus, the difference between the signals detected by the detectors 12 and 14 is hard to distinguish. As a result, the COP may not be distinguished from the actual particle according to the method using the difference between the signals.

FIG. 2B is a graph illustrating a ratio of a light having a wavelength in a narrow band relative to a light having wavelength in a wide band of the light when the oxide layer is formed on the bare wafer. FIG. 2B shows the above-mentioned result. In particular, when the wafer is a recycled wafer, the number of the COPs increases proportional to the number of recycling of the wafer. Accordingly, when the particles on the recycled wafer are monitored, the COP may not be distinctly distinguished from the actual particles so that the particles may not be detected.

A method and an apparatus for detecting particles are disclosed in Japan Laid Open Patent Publication No. 1999-284038. In the method and the apparatus, a light is irradiated to a surface of a silicon wafer. Detectors receive a light scattered from the surface of the wafer in front, rear and upward directions. Although the scattered light is feeble, the COP may be distinguished from the actual particle so that the actual particle may be detected.

FIG. 3 is a cross sectional view illustrating an another conventional apparatus for detecting particles on a wafer.

Referring to FIG. 3, the apparatus includes three detectors having a front channel 32, a center channel 34 and a rear channel 36. The light emitted from a light source 30 is reflected and scattered from a wafer W disposed on a stage 38. The detectors 32, 34 and 36 detect the scattered lights so that the actual particle may be distinguished from the COP using a difference between signals of detected lights.

A significant portion of the lights scattered from the actual particle disposed on the wafer W are mainly oriented to the front and rear channels 32 and 36. The remaining lights are oriented to the center channel 34. On the other hand, the lights scattered from the COP are uniformly oriented to the front, center and rear channels 32, 34 and 36.

To classify the COP on the bare wafer, the following algorithms may be used.

CM>1.14·RM

CM>1.36·FM

In the above algorithms, CM represents a magnitude of a signal outputted from the center channel 34. RM represents a magnitude of a signal outputted from the rear channel 36. FM represents a magnitude of a signal outputted from the front channel 32.

When CM is above 1.4 times RM and is simultaneously above 1.36 times FM, this defect may be classified as the COP. On the contrary, when CM is below 1.4 timed RM and is simultaneously below 1.36 times FM, this defect may be classified as the actual particle.

The above results are illustrated in FIGS. 4A and 4B. FIG. 4A is a graph illustrating a ratio between CM and RM. FIG. 4B is a graph illustrating a ratio between CM and FM.

However, as described above, after the oxide layer is formed on the bare wafer, the relation between the COP and the actual particle does not entirely exist. These results are illustrated in FIGS. 4C and 4D. FIG. 4C is a graph illustrating a ratio between CM and BM. FIG. 4D is a graph illustrating a ratio between CM and FM.

Although the conventional apparatus may distinguish the COP from the actual particle on the bare wafer, the COP may not be distinguished from the actual particle on the wafer having the oxide layer or the nitride layer when employing the above-described conventional apparatus.

SUMMARY OF THE INVENTION

The present invention provides an apparatus for detecting particles on an object capable of distinguishing a critical oriented particle from an actual particle on a wafer regardless of existence of a layer on the wafer.

The present invention provides a method for detecting particles on an object capable of distinguishing a critical oriented particle from an actual particle on wafer regardless of existence of a layer on the wafer.

In accordance with one aspect of the present invention, an apparatus for detecting particles located on an object includes an emitter for irradiating lights to the particles. The object is disposed on a stage in a direction substantially parallel to a surface of the object. The apparatus further includes a driver for generating a relative motion between the emitter and the object for scanning the surface of the object with the lights and a detector for detecting the lights emitted from the emitter or lights scattered from the particle.

In accordance with another aspect of the present invention, an apparatus for detecting particles on an object includes an emitter for irradiating lights to the particles on an object in a direction substantially parallel to a surface of the object. The lights include a first light orienting to a first direction and a second light orienting to a second direction different from the first direction. The apparatus includes a first driver for rotating the emitter relative to the object to irradiate the first and second lights onto the object, and a second driver for moving the emitter relative to the object so as to scan the object by the first and second lights. The apparatus further includes a detector for detecting the first and second lights emitted from the emitter or first and second lights scattered from the particles, and a data processor for analyzing first and second detection signals outputted from the detector and a relative position signal between the emitter and the object. The apparatus may further include a display for displaying the positions of the particles. The object may include a wafer having no patterns thereon. Here, this wafer may include a bare wafer or a wafer having an oxide layer or a nitride layer. The detector may be disposed located in a position which is opposite to the emitter and which is centered on the object. Alternatively, the detector having a dome shape may be disposed over the object. The detector having the dome shape may detect the lights emitted from the emitter or the lights scattered from the particle without failing to detect the particles.

In accordance with one aspect of the present invention, there is provided a method for detecting particles on an object. In the method, lights emitted from an emitter are irradiated to the object in a direction substantially parallel to a surface of the object. A relative linear motion occurs between the emitter and the object to scan the object by the lights. The lights irradiated onto the object or lights scattered from the particle is detected.

In accordance with another aspect of the present invention, there is provided a method for detecting particles on an object. In the method, lights that include a first light orienting to a first direction and a second light orienting to a second direction different from the first direction emitted from an emitter are irradiated onto the object in a direction substantially parallel to a surface of the object. A relative rotary motion occurs between the emitter and the object to irradiate the first and second lights onto the object. A relative linear motion preferably occurs between the emitter and the object to scan the object by the first and second lights. The first and second lights irradiated to the object or first and second lights scattered from the particles are detected. First and second detection signals and a relative position signal between the emitter and the object are analyzed to detect positions of the particles. The positions of the particles may be displayed.

According to an aspect of the present invention, since the lights emitted from the emitter are irradiated in a direction substantially parallel to the surface of the object, the lights may be scattered from the particles to be detected by the detector. However, the lights emitted from the emitter may not be scattered from a critical oriented particle (COP) having a groove formed on the object so that the COP may not be detected. Accordingly, the actual particles on the object may be detected only. The positions of the particles are recognized because the particles are scanned in several directions. Furthermore, the lights emitted from the emitter are irradiated in a direction substantially parallel to the upper surface of the object so that time for scanning the surface of the object may be curtailed. As a result, the particles may be detected quickly so that productivity of semiconductor devices may be improved.

BRIEF DESCRIPTION OF THE DRAWINGS

The above and other features and advantages of the invention will become readily apparent by reference to the following detailed description when considered in conjunction with the accompanying drawings wherein.

DESCRIPTION OF THE PREFERRED EMBODIMENTS

Figure 1:
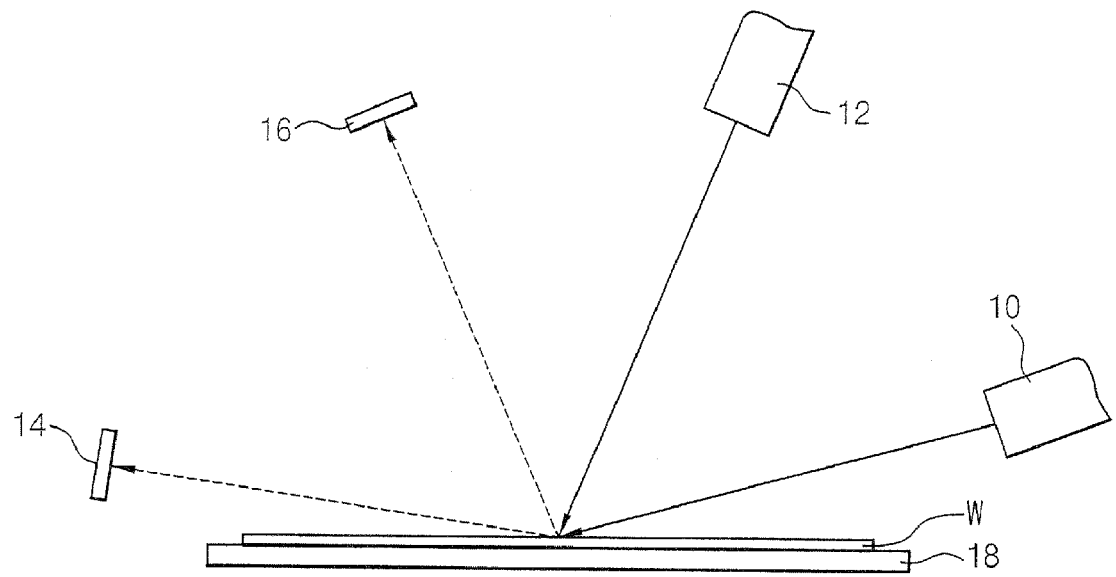
FIG. 1 is a cross sectional view illustrating a conventional apparatus for detecting particles on a wafer.
Figure 2A:
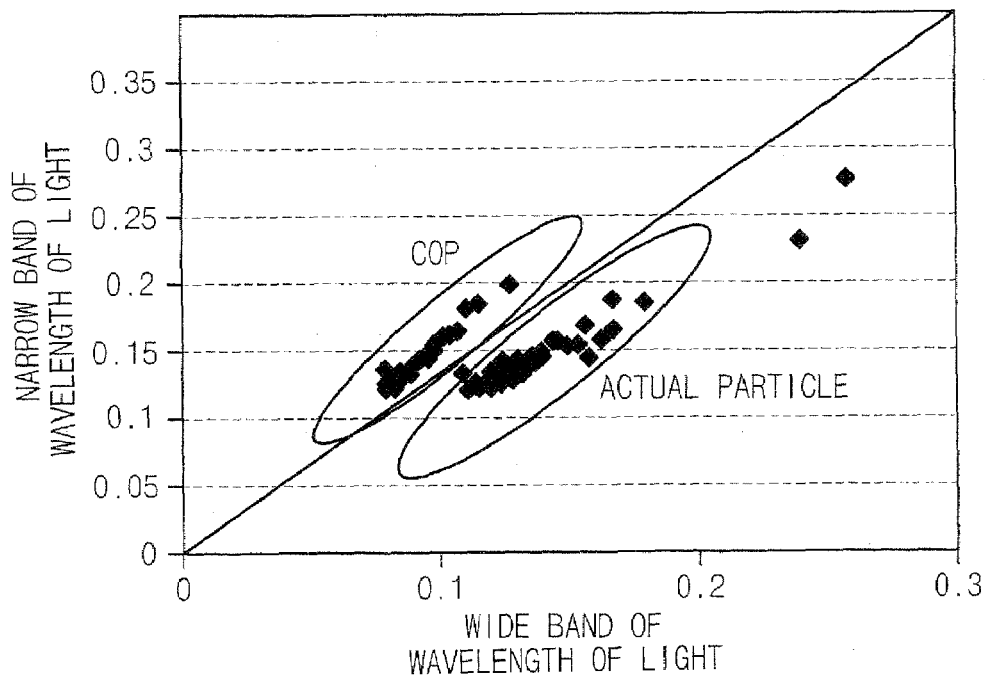
FIGS. 2A and 2B are graphs illustrating results of particle detection using the conventional apparatus of FIG. 1.
Figure 2B:
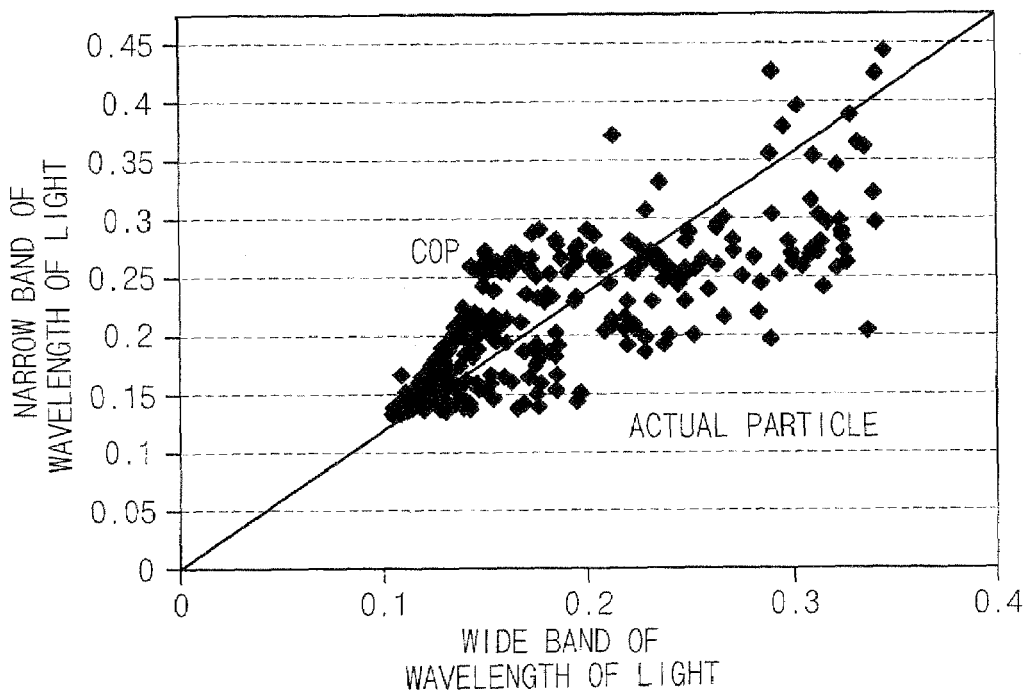
Figure 3:
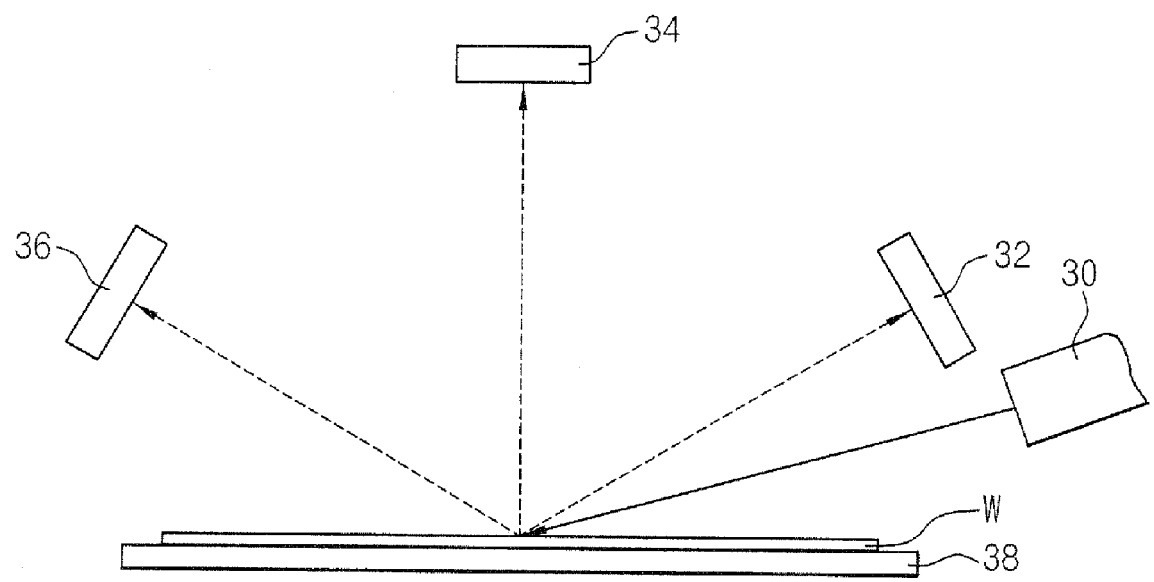
FIG. 3 is a cross sectional view illustrating an another conventional apparatus for detecting particles on a wafer.
Figure 4A:
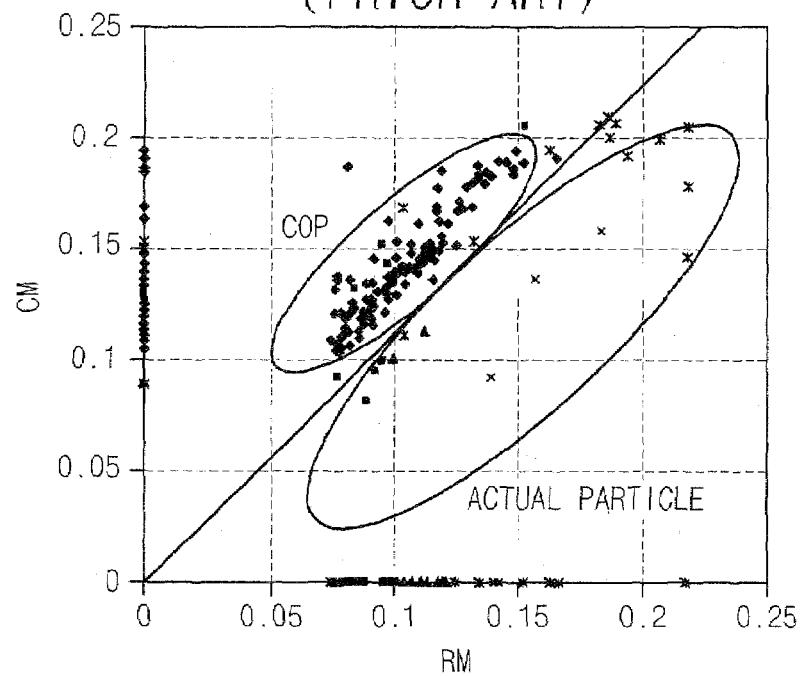
FIGS. 4A and 4B are graphs illustrating results of particle detection using the conventional apparatus of FIG. 3.
Figure 4B:
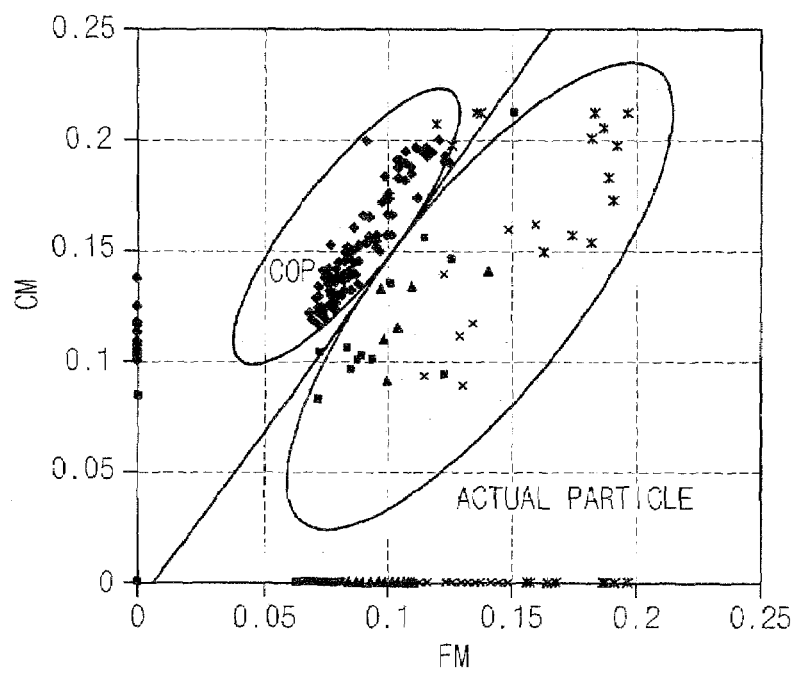
Figure 4C:
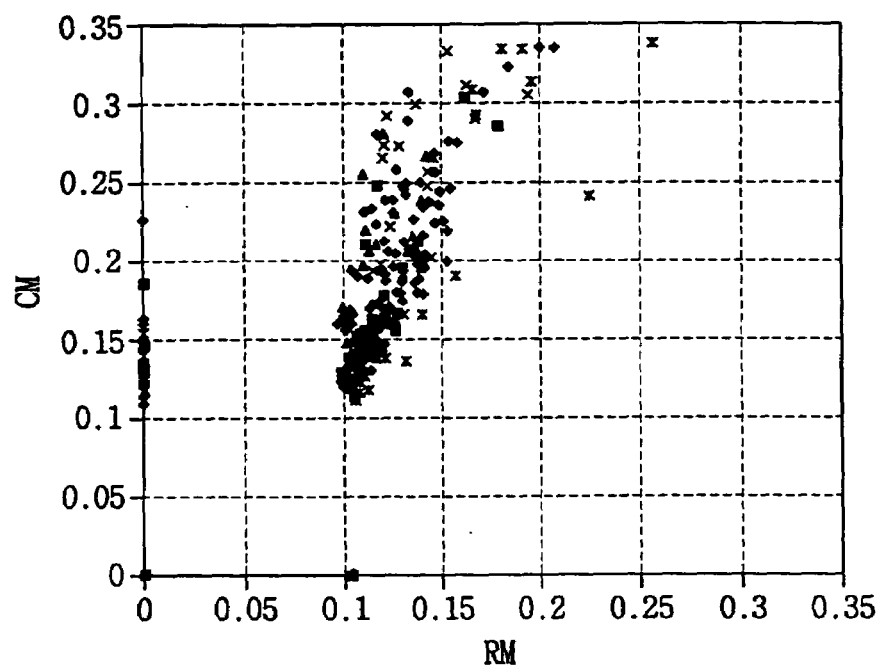
FIG. 4C is a graph illustrating a ratio between CM and BM.
Figure 4D:
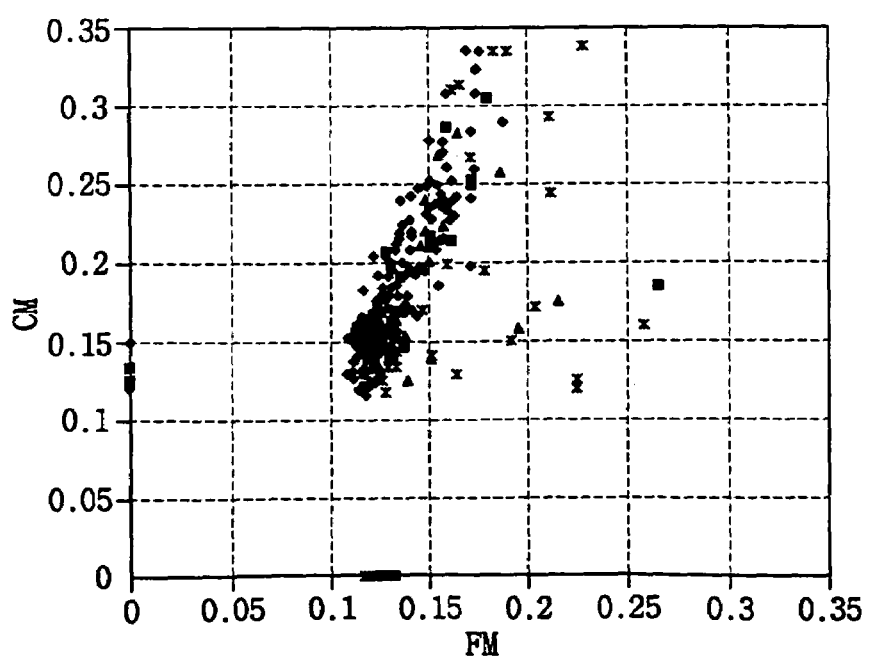
FIG. 4D is a graph illustrating a ratio between CM and FM.

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In the drawings, the thickness of layers and regions are exaggerated for clarity. Like numbers refer to similar or identical elements throughout. It will be understood that when an element such as a layer, region or substrate is referred to as being "on" or "onto" another element, it can be directly on the other element or intervening elements may also be present.

Figure 5A:
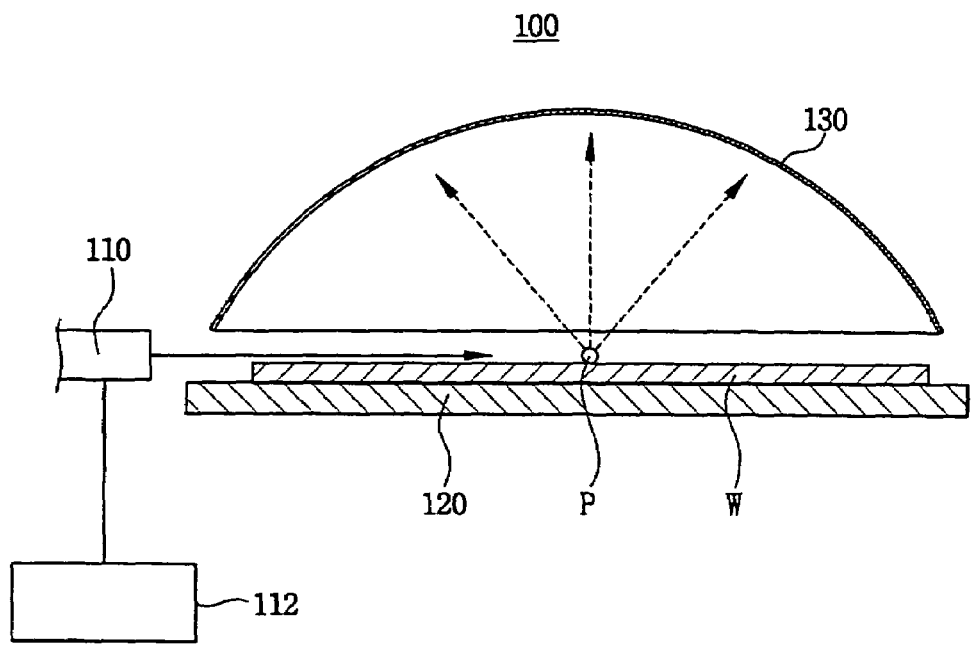
FIG. 5A is a cross sectional view illustrating an apparatus for detecting particles on a wafer according to a first embodiment of the present invention.
Figure 5B:
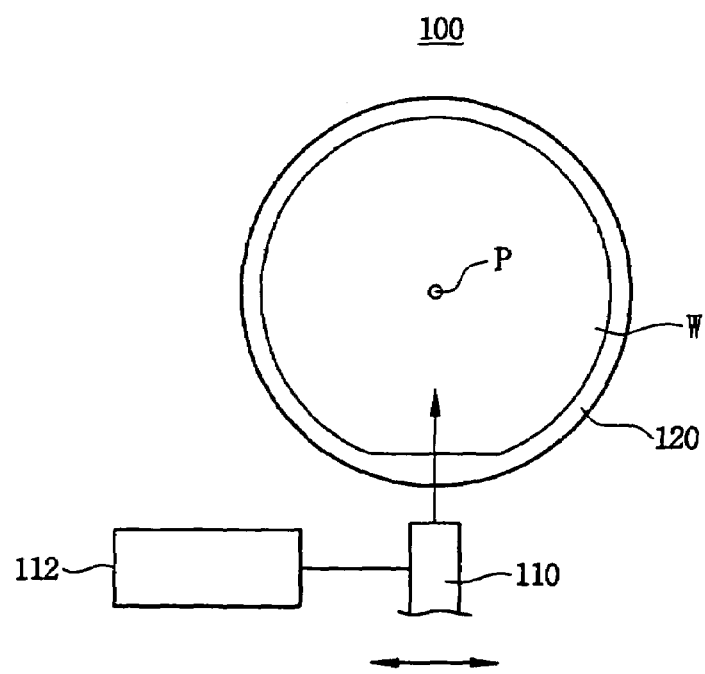
FIGS. 5B and 5C are plan views illustrating an apparatus for detecting particles on a wafer according to the first embodiment of the present invention.

Referring to FIGS. 5A and 5B, an apparatus 100 for detecting particles on a wafer according to the present embodiment includes an emitter 110 for irradiating lights onto an actual particle P formed on a wafer W in a direction substantially parallel to a surface of the wafer W, a driver 112 for moving the emitter 110 in a direction substantially perpendicular to the direction of the lights to scan the wafer W, and a detector 130 for detecting lights scattered from the actual particle P.

The wafer W typically corresponds to a wafer on which a pattern is not formed. This wafer may include a bare wafer formed by a single crystalline growth or a wafer on which a layer such as an oxide layer or a nitride layer is formed. The actual particle P and a critical oriented particle (COP) are formed on the wafer W. Since the actual particle P is positioned on the level surface of the wafer W, the actual particle P may be detected using the apparatus 100. When the wafer includes a patterned wafer, the actual particle P having a size smaller than a line width of the pattern may not be detected using the apparatus 100. The actual wafer P having a size larger than the line width of the pattern may be detected using the apparatus 100.

The emitter 110 irradiates the lights to the actual particle P in a direction parallel to the surface of the wafer W. The lights may include a laser. The laser may include an argon ion laser or a helium laser. These lasers can have a wavelength of about 488 nm. The emitter 110 is disposed substantially parallel to the surface of the wafer W. The lights transmitted substantially parallel to the surface of the wafer W are not reflected from the COP grooved in a V shape on the surface of the wafer W. Accordingly, the lights are only reflected from the actual particle P projected from the surface of the wafer W. As a result, the detector 130 only detects the actual particle P except the COP. Alternatively, the lights may be irradiated substantially parallel to the surface of the wafer W using one or a plurality of mirrors according to the apparatus 100.

The driver 112 is connected to the emitter 110. The driver 112 provides a driving force to the emitter 110 so that the emitter 110 moves in a direction substantially perpendicular to the direction of the lights. Thus, the emitter 110 linearly scans the surface of the wafer W. Furthermore, the emitter 110 may rotatably scan the surface of the wafer W.

Figure 5C:
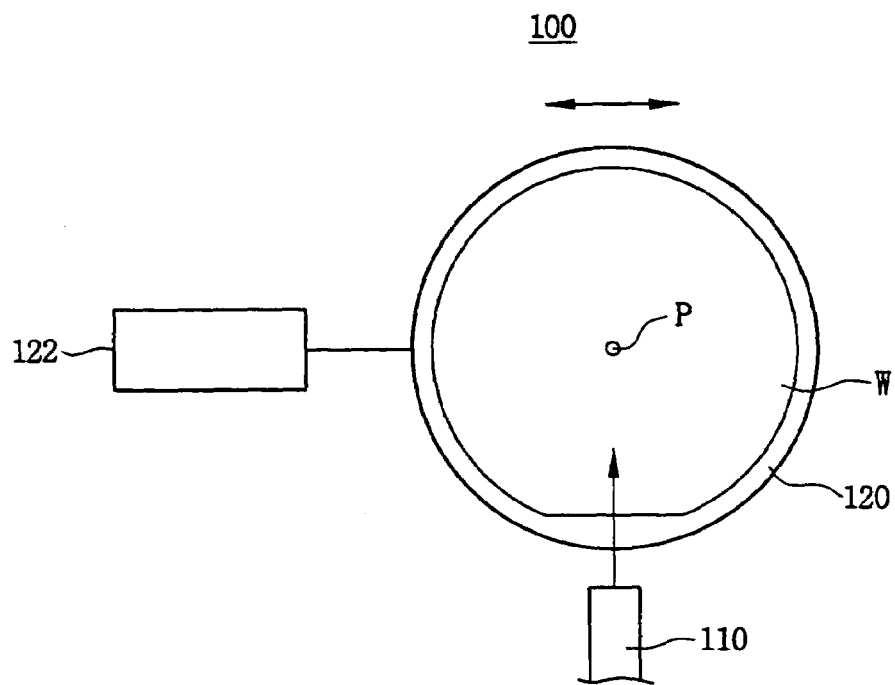

Alternatively, as shown in FIG. 5C, the driver 112 may be connected to a stage 120 on which the wafer W is disposed and fixed. The driver 112 linearly moves the stage 120 while the emitter 110 is stationary. The driver 112 may rotate the stage 120.

Referring again to FIG. 5A, the detector 130 detects lights scattered from the particle P to recognize the actual particle P on the wafer W. The detector 130 has a dome shape to detect the scattered lights. When the actual particle P does not exist on the wafer W, the lights emitted from the emitter 110 are not scattered from the surface of the wafer W. When the actual particle P exists on the wafer W, the lights emitted from the emitter 110 are scattered from the actual particle P on the wafer W so that the detector 130 having the dome shape detects the scattered lights.

When the detector 130 has small area, the detector 130 may not detect the scattered lights or may have difficulty in detecting the scattered lights. Thus, the detector 130 has the dome shape covering the surface of the wafer W. The detector 130 may detect the lights scattered from the particle P in every directions. Since the lights are generally scattered from the particle P in various directions, the detector 130 detects any one light among the scattered lights, thereby recognizing the particle P.

Figure 6:
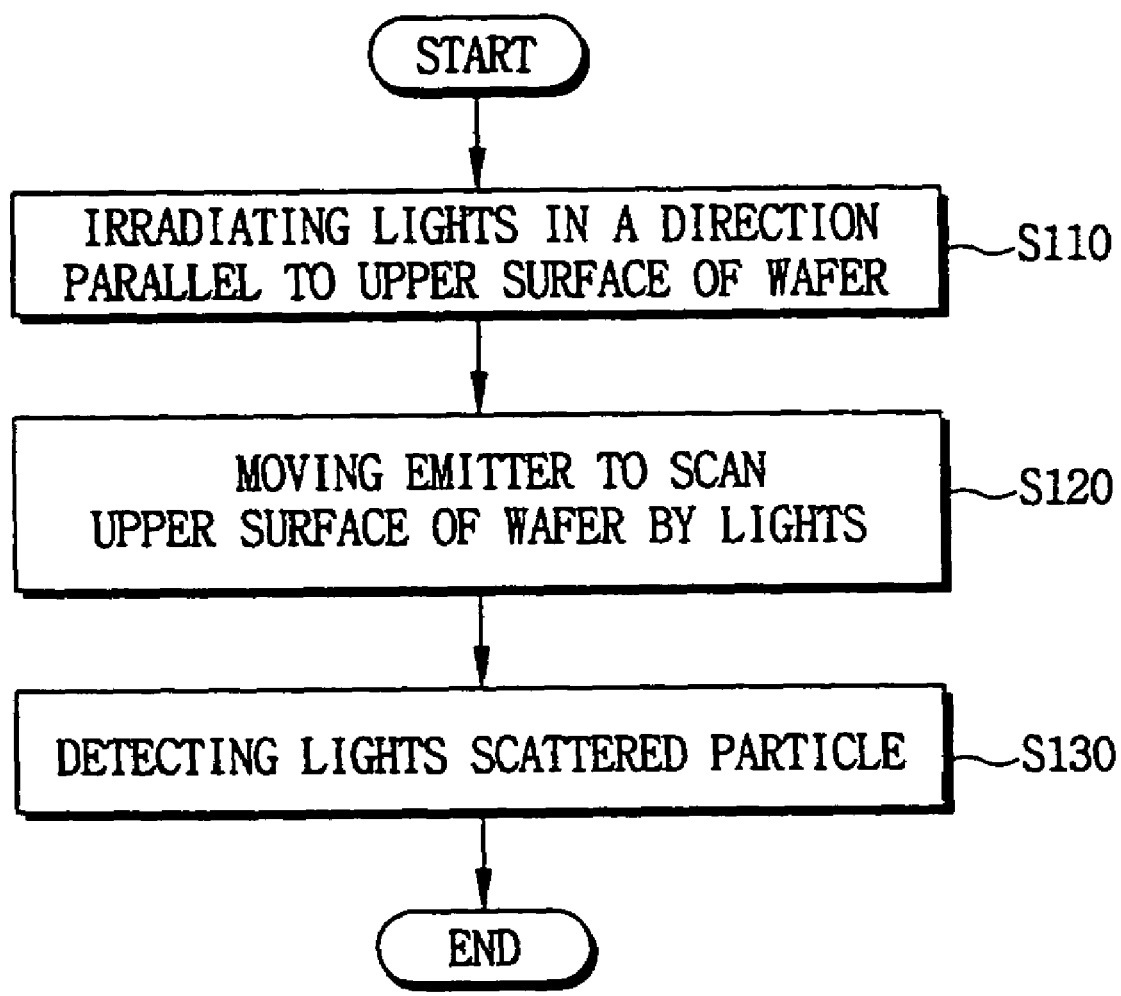
FIG. 6 is a flow chart illustrating a method for detecting particles on a wafer according to the first embodiment of the present invention.

Referring to FIG. 6, in step S110, the emitter 110 irradiates the lights in a direction substantially parallel to the surface of the wafer W.

In step S120, the driver 112 moves the emitter 110 in a direction substantially perpendicular to the direction of the lights to scan the surface of the wafer W.

In step S130, when the lights are scattered from the surface of the wafer W, the detector 130 detects the scattered lights, thereby recognizing the particle P on the wafer W.

Figure 7A:
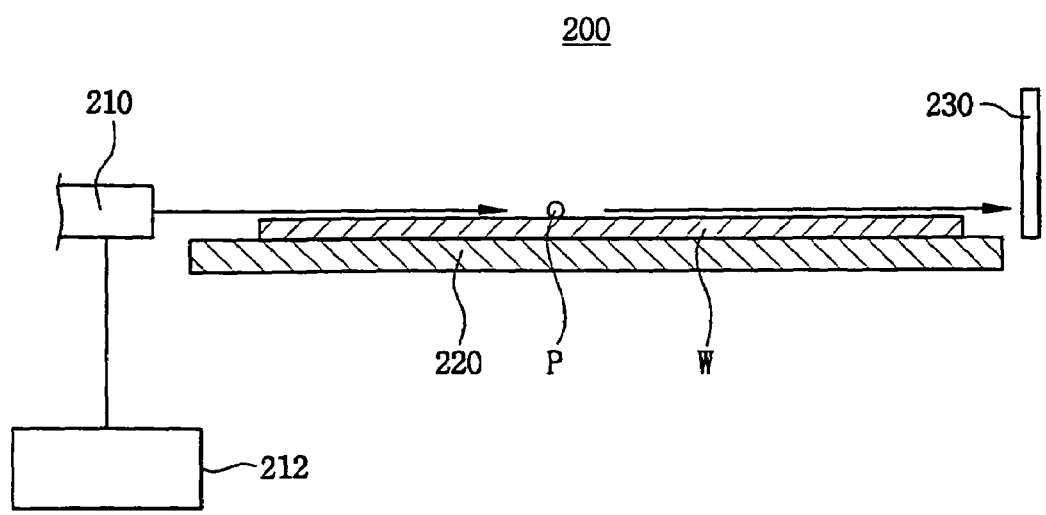
FIG. 7A is a cross sectional view illustrating an apparatus for detecting particles on a wafer according to a second embodiment of the present invention.
Figure 7B:
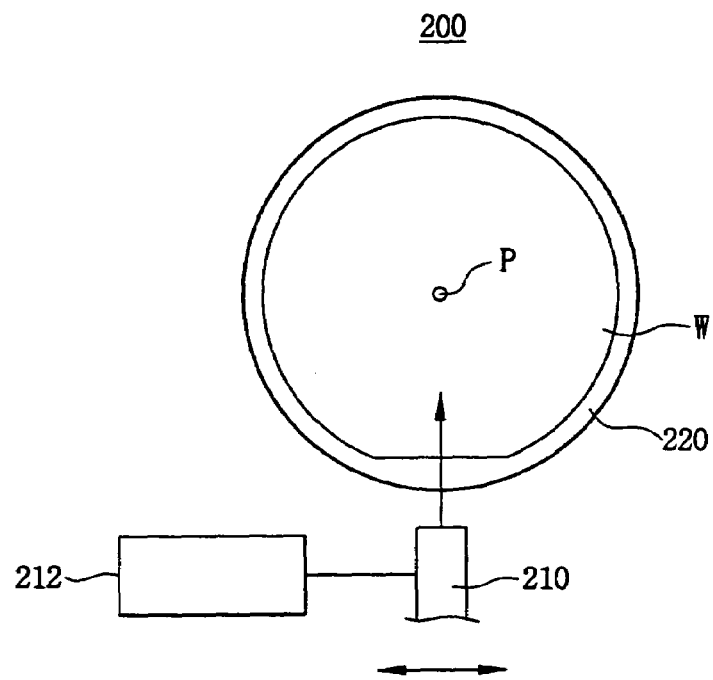
FIGS. 7B and 7C are plan views illustrating an apparatus for detecting particles on a wafer according to the second embodiment of the present invention.

Referring to FIGS. 7A and 7B, an apparatus 200 for detecting particles on a wafer according to present embodiment includes an emitter 210 for irradiating lights to an actual particle P formed on a wafer W in a direction substantially parallel to a surface of the wafer W, a driver 212 for moving the emitter 210 in a direction substantially perpendicular to the direction of the lights to scan the wafer W, and a detector 230 for detecting the lights emitted from the emitter 210.

The emitter 210 irradiates the lights to the actual particle P in a direction substantially parallel to the surface of the wafer W. The emitter 210 is disposed substantially parallel to the surface of the wafer W. The lights which are transmitted substantially parallel to the surface of the wafer W are not reflected from the COP grooved in a V shape on the surface of the wafer W.

Figure 7C:
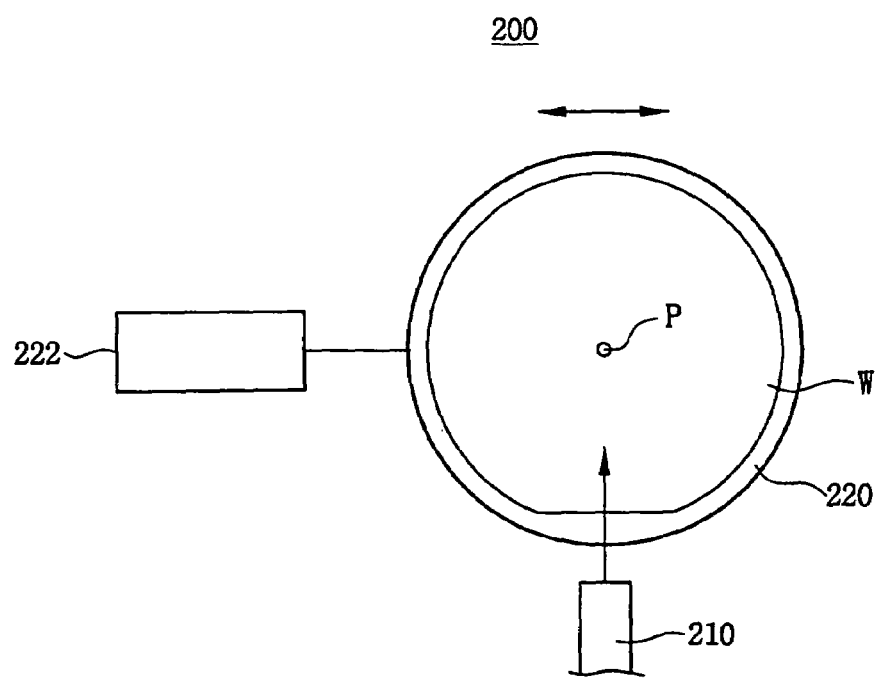

The driver 212 is connected to the emitter 210. The driver 212 provides a driving force to the emitter 210 so that the emitter 210 moves in a direction substantially perpendicular to the direction of the lights. Thus, the emitter 210 linearly scans the surface of the wafer W. Meanwhile, the emitter 210 may rotatably scan the surface of the wafer W. Alternatively, as shown in FIG. 7C, the driver 212 may be connected to a stage 220 on which the wafer W is disposed and fixed. The driver 212 linearly moves the stage 220 while the emitter 210 is stationary. The driver 212 may rotate the stage 220.

Referring again to FIG. 7A, the detector 230 is disposed opposite to the emitter 210 centering on the stage 220 to detect lights emitted from the emitter 210. To detect the emitted lights, the detector 230 has a plate shape. When the actual particle P exists on the wafer W, the lights emitted from the emitter 210 are scattered from the particle P so that the detector 230 which has a plate shape does not detect the scattered lights. When the actual particle P does not exist on the wafer W, the lights emitted from the emitter 210 are directly irradiated to the detector 230. That is, when the detector 230 detects the lights, it is acknowledged that the particle P does not exist on the wafer W. On the contrary, when the detector 230 does not detect the lights, it is acknowledged that the particle P exists on the wafer W.

Figure 8A:
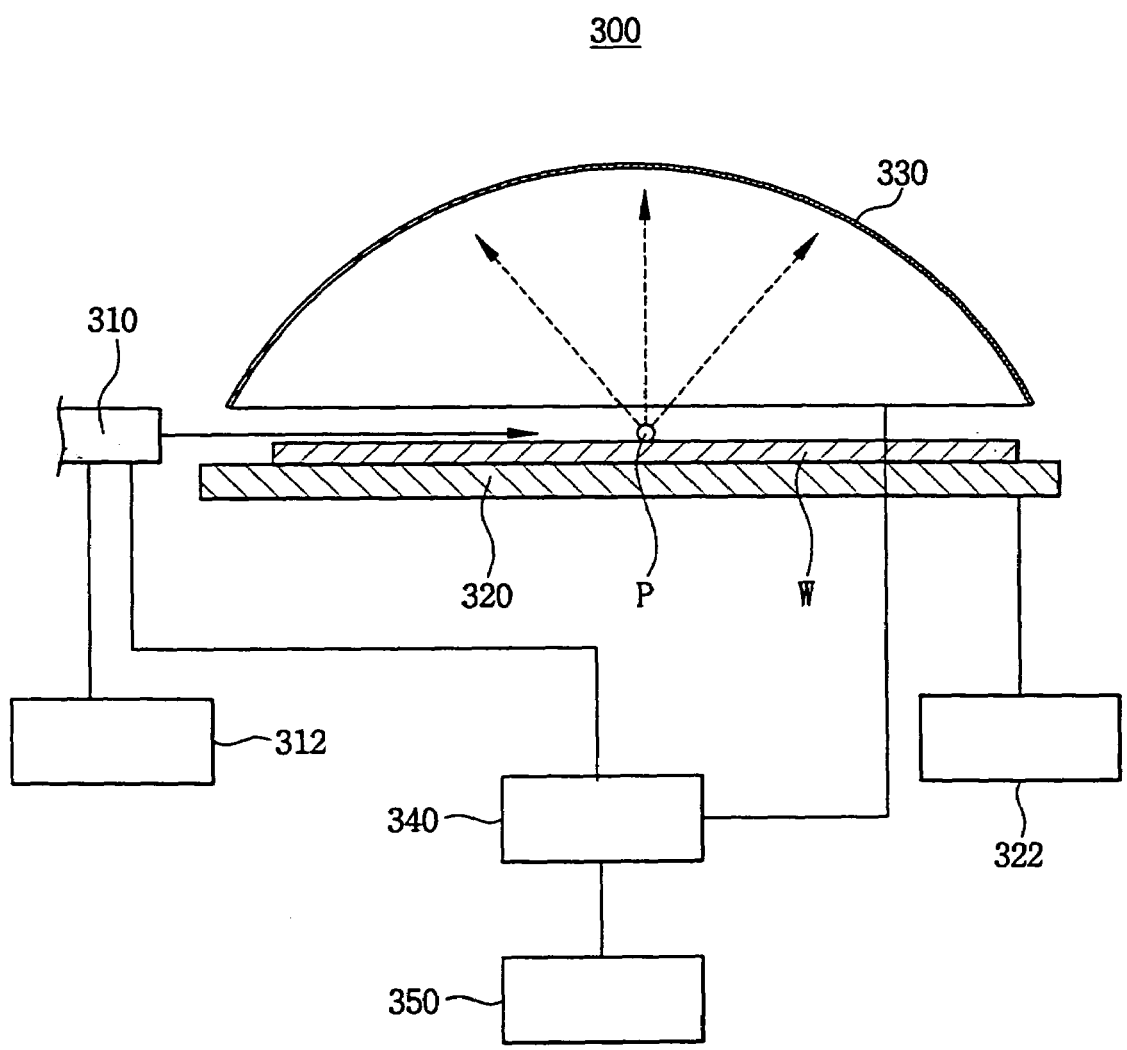
FIG. 8A is a cross sectional view illustrating an apparatus for detecting particles on a wafer according to a third embodiment of the present invention.
Figure 8B:
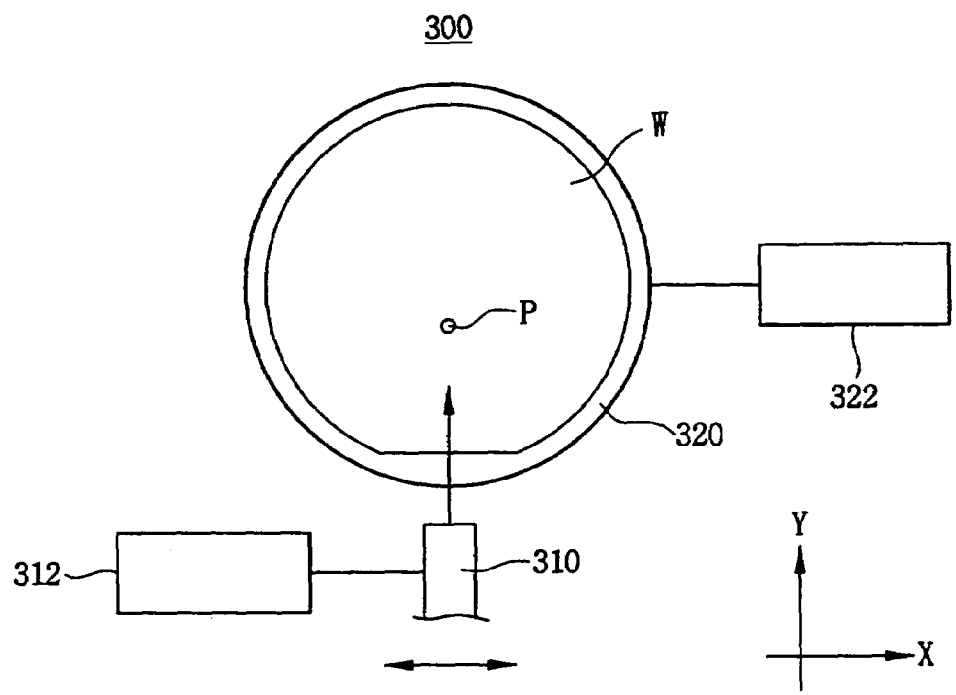
FIGS. 8B and 8C are plan views illustrating an apparatus for detecting particles on a wafer according to the third embodiment of the present invention.

Referring to FIGS. 8A and 8B, an apparatus 300 for detecting particles on a wafer according to a third embodiment includes an emitter 310 for irradiating first and second lights to an actual particle P formed on a wafer W in a direction substantially parallel to a surface of the wafer W, a first driver 322 for rotating a stage 320 on which the wafer W is disposed, a second driver 312 for moving the emitter 310 in a direction substantially perpendicular to the directions of the first and second lights so as to scan the wafer W by the first and second lights, a detector 330 for detecting first and second lights scattered from the actual particle P, a data processor 340 for detecting position of the particle P by analyzing a signal from the detector 330, and a display 350 for displaying the position of the particle P.

The wafer W may correspond to a wafer on which a pattern is not formed. This wafer may include a bare wafer produced through a single crystalline growth or a wafer on which a layer, for example, an oxide layer or a nitride layer, is formed. The actual particle P and a critical oriented particle (COP) are formed on the wafer W. Since the actual particle P is positioned on a surface of the wafer W, and the actual particle P may be detected using the apparatus 300. When the wafer is a patterned wafer, the actual particle P has a size smaller than a line width of the pattern which may not be detected using the apparatus 300. The actual wafer P has a size larger than the line width of the pattern and may be detected using the apparatus 300.

Figure 8C:
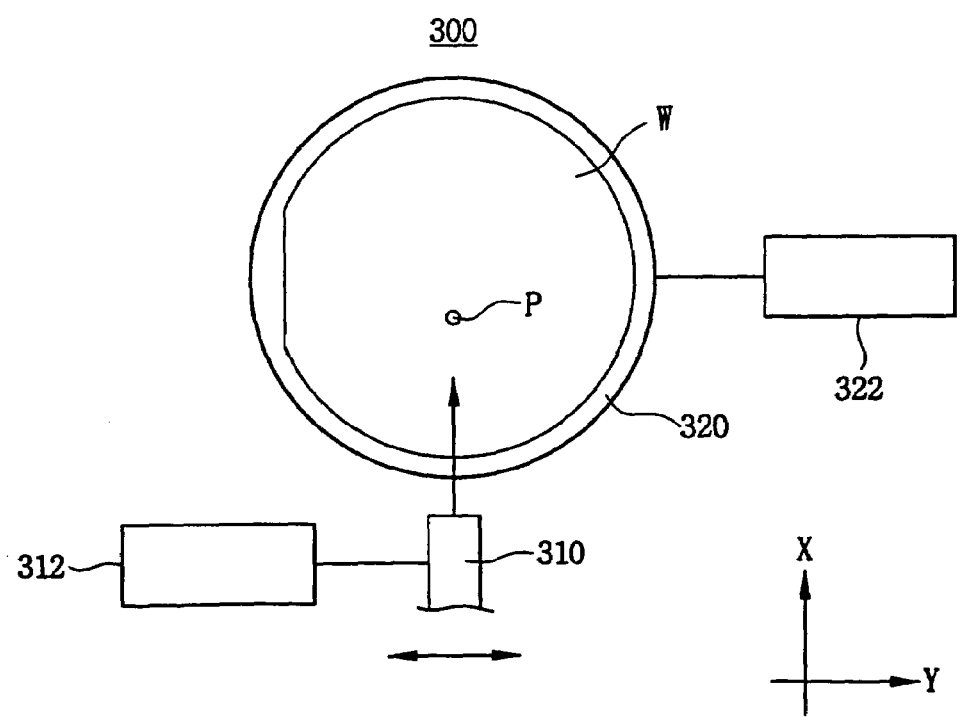

The wafer W is aligned using a pre-aligner (not shown). With reference to FIG. 8B, the aligned wafer W is disposed on the stage 320. A flat zone of the wafer W is substantially perpendicular to the direction of the transmission of first and second lights. Alternatively, with reference to FIG. 8C, the flat zone of the wafer W may be substantially perpendicular to the direction of the transmission of the first and second lights. In FIGS. 8B and 8C, a Y-axis is substantially perpendicular to the flat zone of the wafer W and also passes through the center of the wafer W. An X-axis is substantially perpendicular to the Y-axis and also passes through the center of the wafer W. The X-axis and the Y-axis are included in a plane that is substantially parallel to the surface of the wafer W and includes the particle P on the wafer W.

The emitter 310 irradiates the first and second lights to the actual particle P in a direction substantially parallel to the surface of the wafer W. The first and second lights may include a laser. The emitter 310 is disposed substantially parallel to the surface of the wafer W. The first and second lights are transmitted substantially parallel to the surface of the wafer W, and are not reflected from the COP grooved in a V shape on the surface of the wafer W. Accordingly, the first and second lights are only reflected from the actual particle P and are projected from the surface of the wafer W. As a result, the detector 330 only detects the actual particle P except for the COP.

The second driver 312 is connected to the emitter 310. The second driver 312 provides a driving force to the emitter 310 so that the emitter 310 moves in a direction perpendicular to the directions of the first and second lights. Thus, the emitter 310 linearly scans the surface of the wafer W in the direction of the X-axis and the Y-axis.

The first driver 322 is connected to the stage 320 on which the wafer W is disposed and fixed. The first driver 322 rotates the stage 320. Since the first driver 322 rotates the stage 320, the emitter 310 may irradiate the first and second lights in various directions to detect the particle P by the detector 330. To detect the particle P, and to recognize the position of the particle P using a perpendicular coordinate system having an X-axis and a Y-axis, the first driver 322 rotates the stage 320 in a clockwise or counterclockwise direction through an angle of about 90°.

The detector 330 detects lights scattered from the particle P to recognize the actual particle P on the wafer W. The detector 330 has a dome shape to detect the scattered lights. The detector 330 detects a first light scattered from the particle P on the surface of the wafer W which is scanned by the first emitted light along the X-axis. The detector 330 also detects a second light scattered from particle P on the surface of the wafer W which is scanned by the second emitted light along the Y-axis. When the actual particle P does not exist on the wafer W, the first and second lights emitted from the emitter 310 are not scattered from the surface of the wafer W. When the actual particle P exists on the wafer W, the first and second lights emitted from the emitter 310 are scattered from the actual particle P on the wafer W so that the detector 330 having the dome shape detects the scattered first and second lights.

When the detector 330 has small area, the detector 330 may not detect the scattered lights or may have difficulty in detecting the scattered lights. Thus, the detector 330 has the dome shape covering the surface of the wafer W. The detector 330 may detect the lights scattered from the particle P in every directions. Since the lights are generally scattered from the particle P in various directions, the detector 330 detects any single light among the scattered lights, thereby recognizing the particle P.

The data processor 340 is connected to the emitter 310 and the detector 330, respectively. The data processor 340 receives first and second detection signals generated from the detector 330 that correspond to the first and second scattered lights. The data processor 340 also receives a relative position signal between the wafer W and the emitter 310 outputted from the detector 330. The position of the particle P is recognized on the perpendicular coordinate system using the first and second detection signals and the position signal.

The display 350 displays the position of the particle P on the wafer W using the X and Y coordinates of the particle P.

Figure 9:
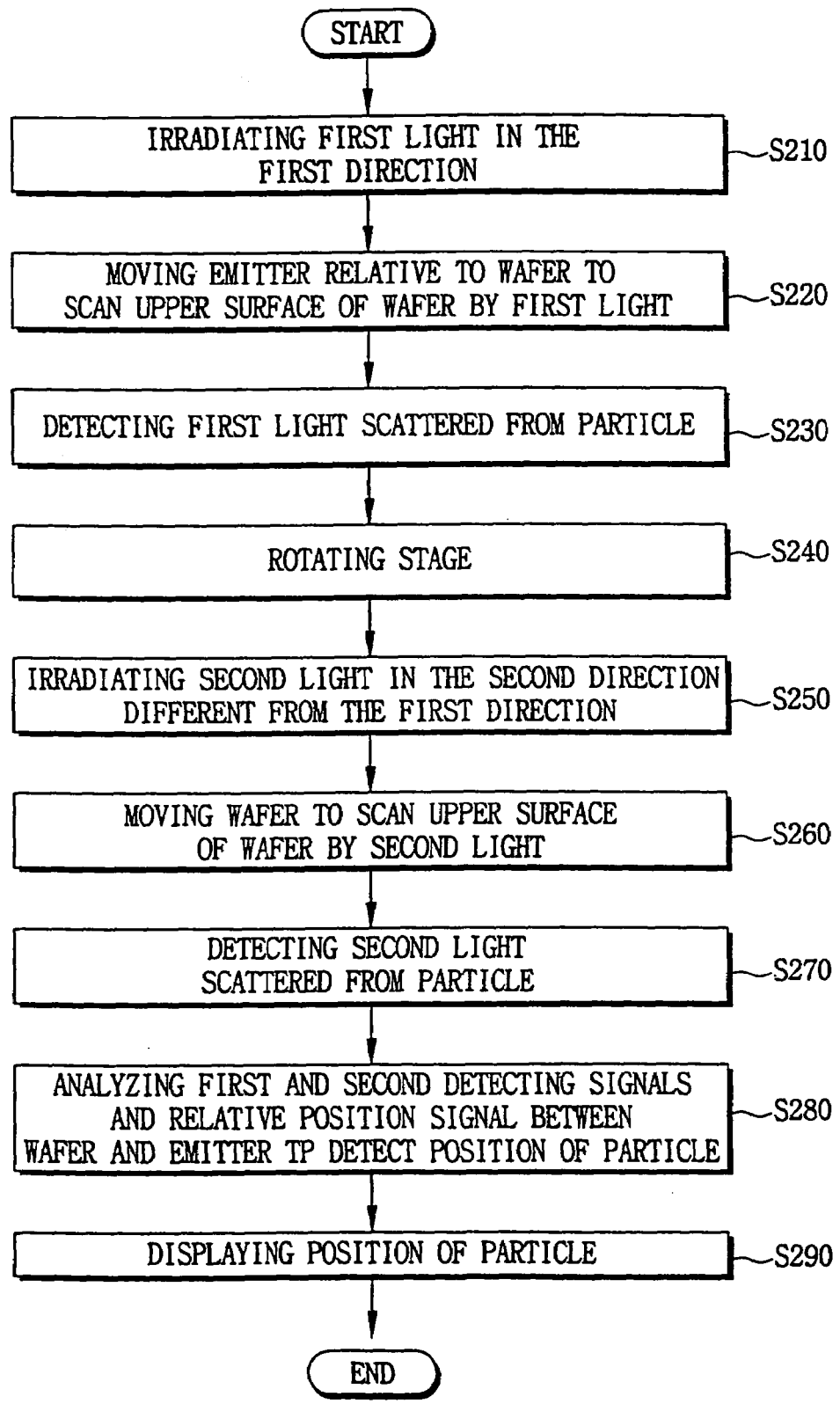
FIG. 9 is a flow chart illustrating a method for detecting particles on a wafer according to the third embodiment of the present invention.

Referring to FIG. 9, a pre-aligner aligns a flat zone of the wafer W. The wafer W is disposed on the stage 320. The flat zone of the wafer W is substantially perpendicular to the directions of lights. In step S210, the emitter 310 irradiates a first light in a first direction substantially parallel to the Y-axis.

In step S220, the second driver 312 moves the emitter 310 to scan the surface of the wafer W by the first emitted light along the X-axis.

In step S230, the detector 330 detects a first light scattered from the particle P.

In step S240, the first driver 322 rotates the stage 320 by an angle of up to about 90° in a clockwise direction or a counterclockwise direction.

In step S250, the emitter 310 irradiates a second light in a second direction substantially parallel to the X-axis.

In step S260, the second driver 312 moves the emitter 310 to scan the surface of the wafer W by the second emitted light along the Y-axis.

In step S270, the detector 330 detects a second light scattered from the particle P. The detector 330 generates a first detection signal corresponding to the first scattered light, a second detection signal corresponding to the second scattered light, and a relative position signal between the wafer W and the emitter 310.

In step S280, the data processor 340 analyzes the first and second detection signals and the position signal to recognize an X and a Y coordinates of the particle P.

In step S290, the display 350 displays the X and Y coordinates of the particle P.

Figure 10:
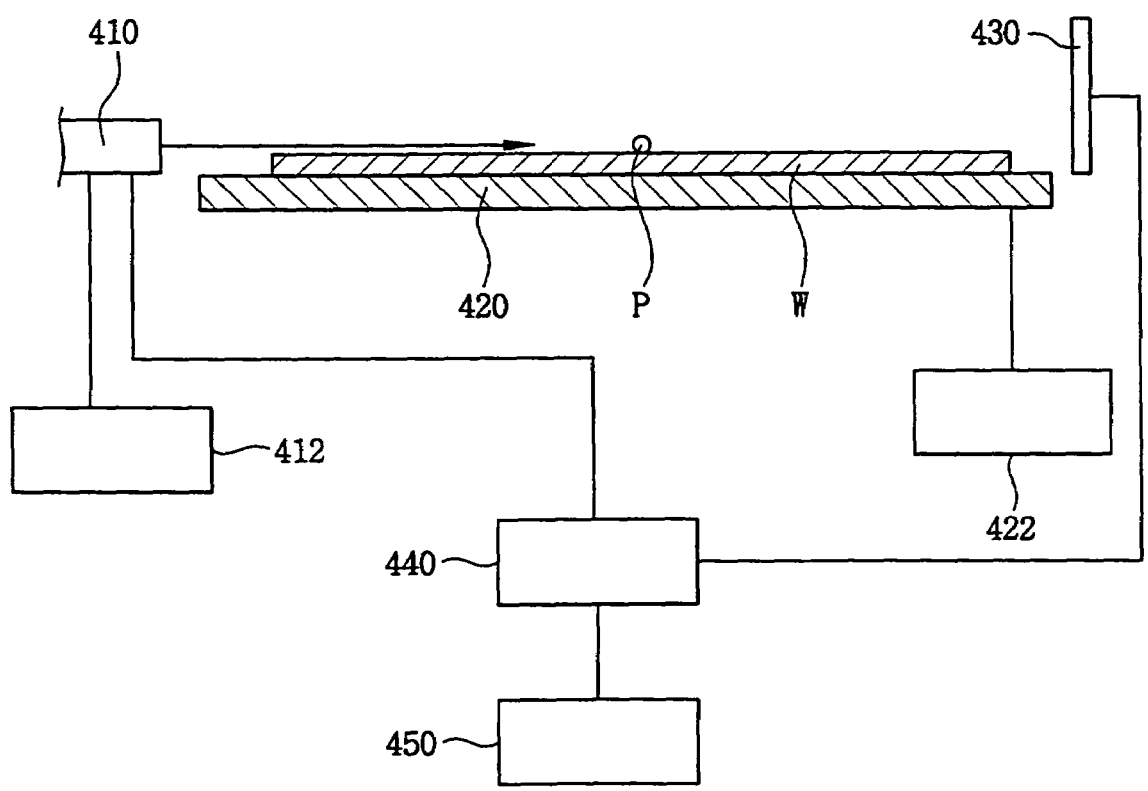
FIG. 10 is a cross sectional view illustrating an apparatus for detecting particles on a wafer according to a fourth embodiment of the present invention.

Referring to FIG. 10, an apparatus 400 for detecting particles on a wafer according to the present embodiment includes an emitter 410 for irradiating first and second lights to an actual particle P on a wafer W in a direction substantially parallel to a surface of the wafer W, a first driver 422 for rotating a stage 420 on which the wafer W is disposed, a second driver 412 for moving the emitter 410 in a direction substantially perpendicular to the directions of the first and second lights so as to scan the wafer W, a detector 430 for detecting the first and second lights, a data processor 440 for detecting position of the particle P by analyzing a signal from the detector 430, and a display 450 for displaying a position of the particle P.

The emitter 410 irradiates the first and second lights to the actual particle P in a direction substantially parallel to the surface of the wafer W. The emitter 410 is disposed substantially parallel to the surface of the wafer W. The first and second lights substantially parallel to the surface of the wafer W are not reflected from the COP grooved in a V shape on the surface of the wafer W. Accordingly, the first and second lights are only reflected from the actual particle P which is projected from the surface of the wafer W. As a result, the detector 430 only detects the actual particle P besides the COP.

The second driver 412 is connected to the emitter 410. The second driver 412 provides a driving force to the emitter 410 so that the emitter 410 moves in a direction substantially perpendicular to the directions of the first and second lights. The first driver 422 is connected to the stage 420 on which the wafer W is disposed and fixed. The first driver 422 rotates the stage 420.

The detector 430 is disposed opposite to the emitter 410 centering on the stage 420 to detect lights emitted from the emitter 410. The detector 430, which preferably has a plate shape, detects the emitted lights. When the actual particle P exists on the wafer W, the lights emitted from the emitter 410 are scattered from the particle P so that the detector 430 does not detect the scattered lights. When the actual particle P does not exist on the wafer W, the lights emitted from the emitter 410 are directly irradiated to the detector 430. That is, when the detector 430 detects the lights, it is acknowledged that the particle P does not exist on the wafer W. On the other hand, when the detector 430 does not detect the lights, it is acknowledged that the particle P exists on the wafer W.

The data processor 440 is connected to the emitter 410 and the detector 430, respectively. The data processor 440 receives first and second detection signals outputted from the detector 430 that correspond to the first and second scattered lights. Also, the data processor 440 receives a relative position signal between the wafer W and the emitter 410 outputted from the detector 430. The position of the particle P is recognized in a perpendicular coordinate using the first and second detection signals and the position signal. The display 450 shows the position of the particle P on the wafer W using an X and a Y coordinates of the particle P.

Figure 11A:
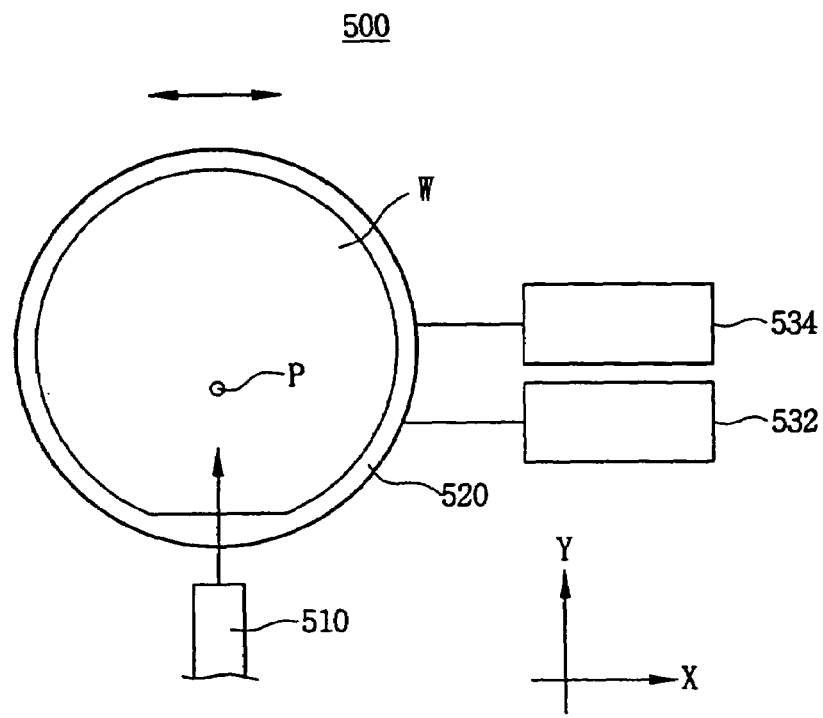
FIGS. 11A and 11B are plan views illustrating an apparatus for detecting particles on a wafer according to a fifth embodiment of the present invention.

Referring to FIG. 11A, an apparatus 500 for detecting particles on a wafer according to the present embodiment includes an emitter 510 for irradiating first and second lights to an actual particle P on a wafer W in a direction parallel to a surface of the wafer W, a first driver 532 for rotating a stage 520 on which the wafer W is disposed, a second driver 534 for moving the stage 520 in a direction perpendicular to the directions of the first and second lights so as to scan the wafer W by the first and second lights, a detector (not shown) for detecting the first and second lights, a data processor (not shown) for detecting position of the particle P by analyzing a signal from the detector, and a display (not shown) for displaying s position of the particle P.

The wafer W is disposed on the stage 520. A flat zone of the wafer W is perpendicular to the directions of the first and second lights.

The second driver 534 is connected to the stage 520. The second driver 534 provides a driving force to the stage 520 so that the stage 520 moves along an X-axis perpendicular to the directions of the first and second lights. The first driver 532 is connected to the stage 520 on which the wafer W is disposed and fixed. The first driver 532 rotates the stage 520.

Figure 11B:
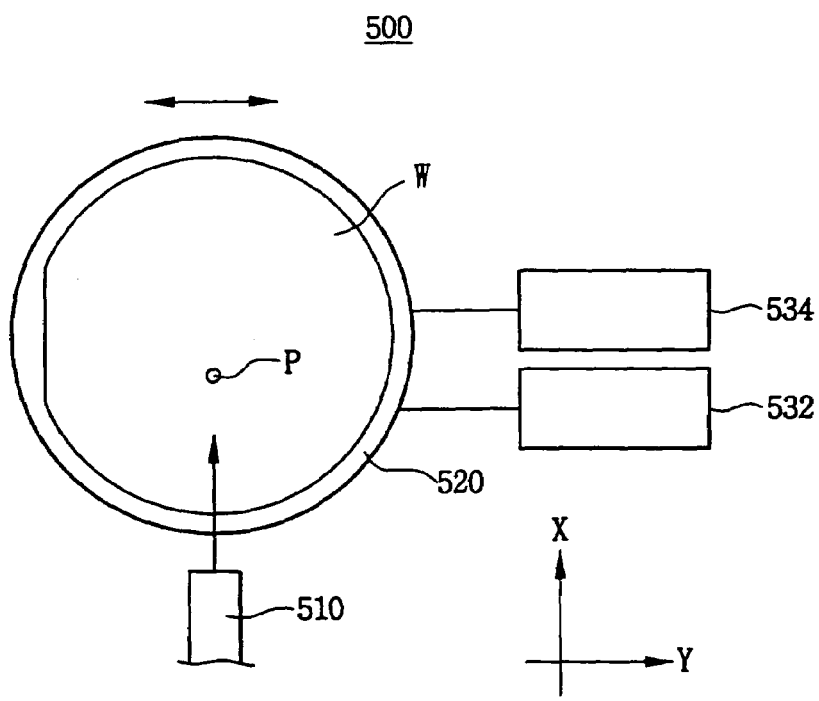

Alternatively, as shown in FIG. 11B, the flat zone of the wafer may be parallel to the directions of the first and second lights. The second driver 532 may move the stage 520 along a Y-axis.

Figure 12A:
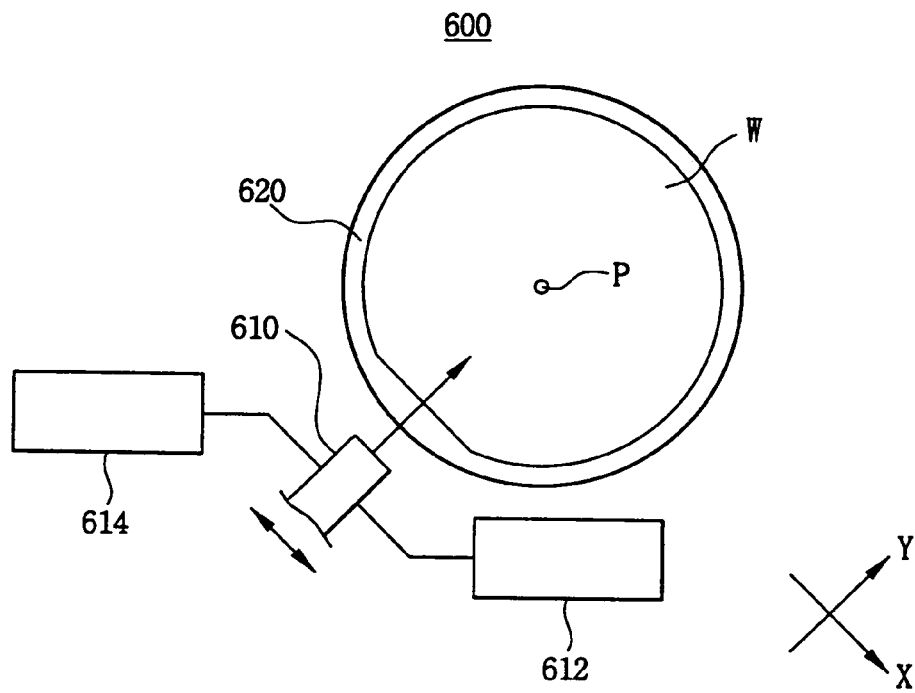
FIGS. 12A and 12B are plan views illustrating an apparatus for detecting particles on a wafer according to a sixth embodiment of the present invention.

Referring to FIG. 12A, an apparatus 600 for detecting particles on a wafer according to the present embodiment includes an emitter 610 for irradiating first and second lights to an actual particle P on a wafer W in a direction substantially parallel to a surface of the wafer W, a first driver 622 for rotating the emitter 610, a second driver 612 for moving the emitter 610 in a direction substantially perpendicular to the directions of the first and second lights in order to scan the wafer W by the first and second lights, a detector (not shown) for detecting the first and second lights, a data processor (not shown) for detecting position of the particle P by analyzing a signal from the detector, and a display (not shown) for displaying a position of the particle P.

The wafer W is disposed on the stage 620. A flat zone of the wafer W is substantially perpendicular to the directions of the first and second lights.

The second driver 612 is connected to the emitter 610. The second driver 612 provides a driving force to the emitter 610 so that the emitter 610 moves along an X-axis substantially perpendicular to the directions of the first and second lights. The first driver 622 is connected to the emitter 610. The first driver 622 rotates the emitter 610.

Figure 12B:
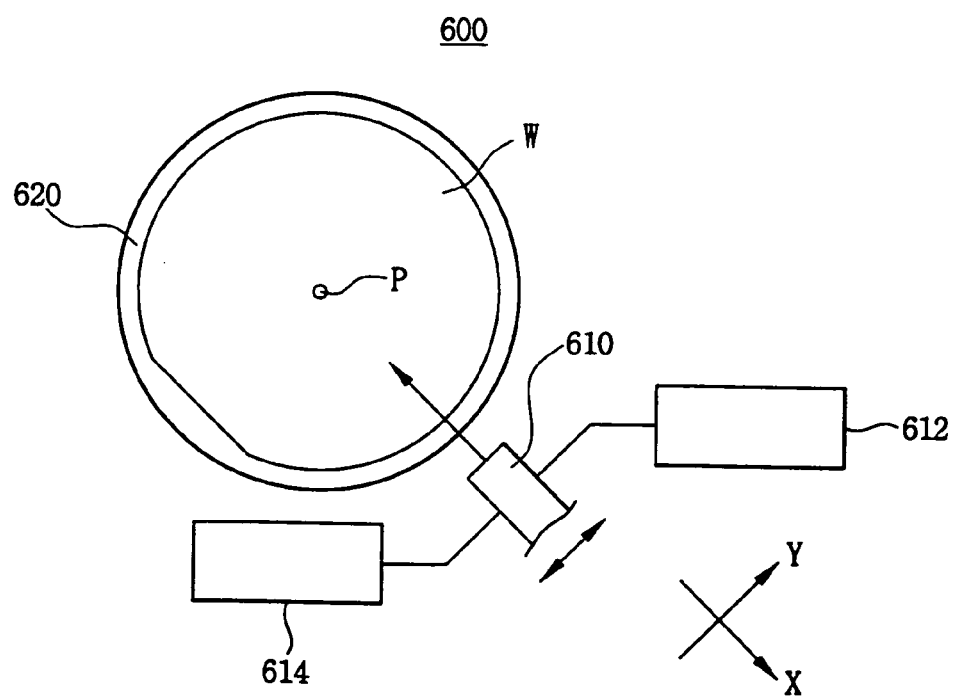

Alternatively, as shown in FIG. 12B, the flat zone of the wafer W may be substantially parallel to the directions of the first and second lights. The second driver 612 may move the stage 620 along a Y-axis.

Figure 13A:
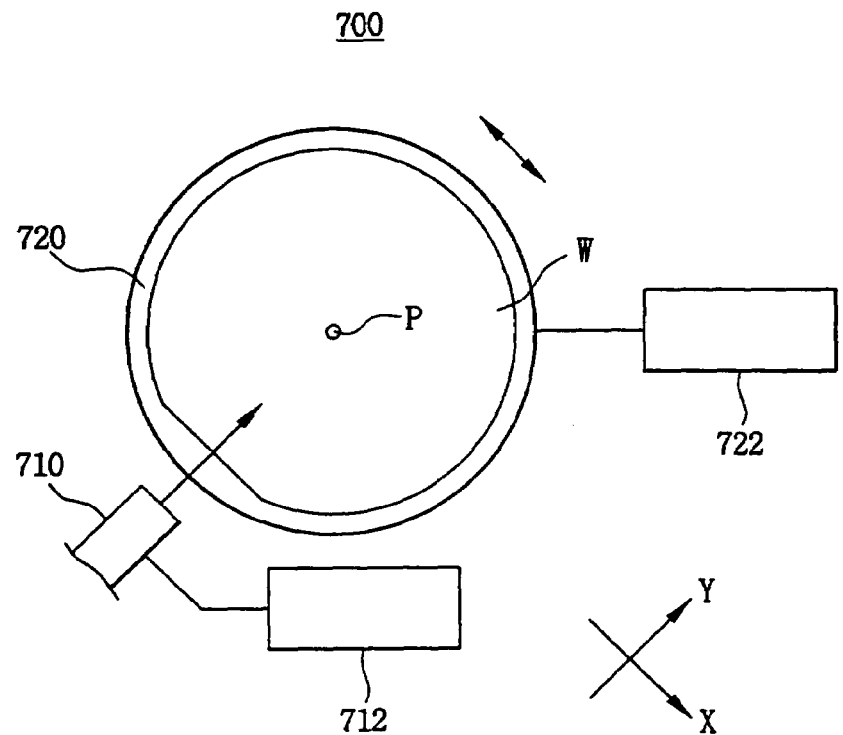
FIGS. 13A and 13B are plan views illustrating an apparatus for detecting particles on a wafer according to a seventh embodiment of the present invention.

Referring to FIG. 13A, an apparatus 700 for detecting particles on a wafer according to the present embodiment includes an emitter 710 for irradiating first and second lights to an actual particle P on a wafer W in a direction substantially parallel to a surface of the wafer W, a first driver 722 for rotating the emitter 710, a second driver 712 for moving the stage 710 in a direction substantially perpendicular to the directions of the first and second lights in order to scan the wafer W, a detector (not shown) for detecting the first and second lights, a data processor (not shown) for detecting position of the particle P by analyzing a signal from the detector, and a display (not shown) for displaying a position of the particle P.

The wafer W is disposed on the stage 720. A flat zone of the wafer W is substantially perpendicular to the directions of the first and second lights.

The second driver 712 is connected to the stage 720. The second driver 712 provides a driving force to the stage 720 so that the stage 720 moves along an X-axis substantially perpendicular to the directions of the first and second lights. The first driver 722 is connected to the emitter 710. The first driver 722 rotates the emitter 710.

Figure 13B:
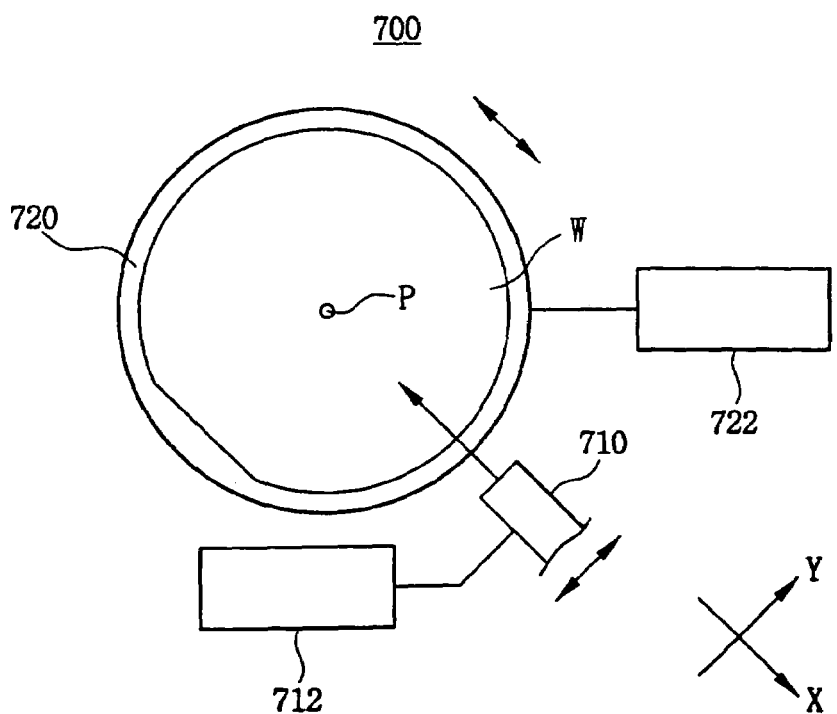

Alternatively, as shown in FIG. 13B, the flat zone of the wafer W may be substantially parallel to the directions of the first and second lights. The second driver 712 may move the stage 720 along a Y-axis.

Figure 14A:
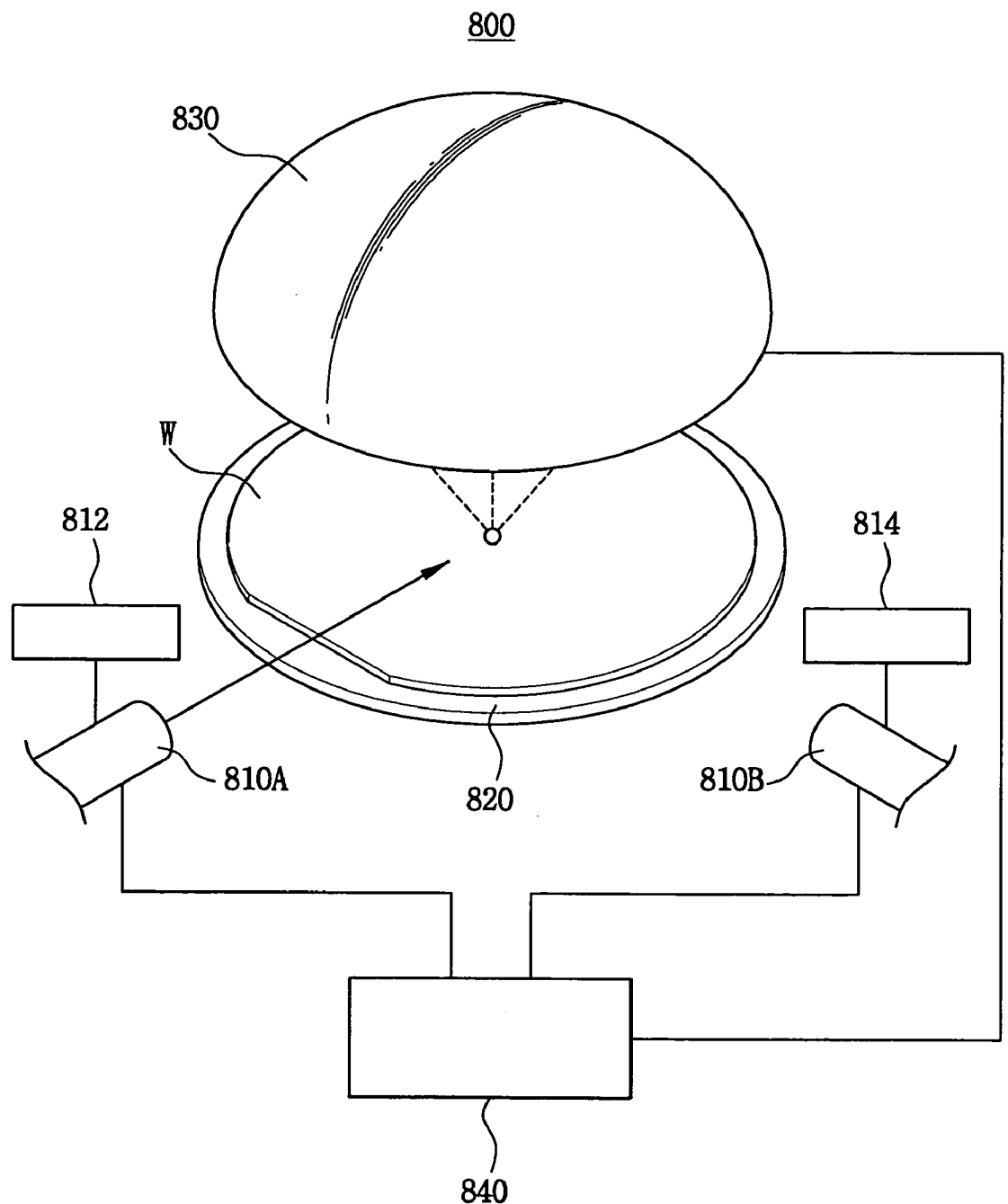
FIG. 14A is a perspective view illustrating an apparatus for detecting particles on a wafer according to an eighth embodiment of the present invention.

Referring to FIG. 14A, an apparatus 800 for detecting particles on a wafer according to the present embodiment includes a first emitter 810a for irradiating a first light to an actual particle P formed on a wafer W in a first direction substantially parallel to a surface of the wafer W, and a second emitter 810b for irradiating a second light to the actual particle P on the wafer W in a second direction substantially parallel to the surface of the wafer W. The second direction is different from the first direction.

The apparatus 800 further includes a first driver 812 for moving the first emitter 810a in a third direction substantially perpendicular to the first direction to scan the surface of the wafer W, and a second driver 814 for moving the second emitter 810b in a fourth direction substantially perpendicular to the second direction to scan the surface of the wafer W by the second light.

In addition, the apparatus 800 includes a detector 830 for detecting first and second lights scattered from the actual particle P, and a data processor 840 for detecting a position of the particle P by analyzing first and second detection signals from the detector 830. The data processor 840 additionally analyzes the first and second position signals of the first and second emitters 810a and 810b to detect the position of the particle P.

The wafer W typically does not include a pattern formed thereon. Further illustrations of the wafer W are omitted. The wafer W is disposed on the stage 820. A flat zone of the wafer W is substantially perpendicular to the directions of the first light.

Figure 14B:
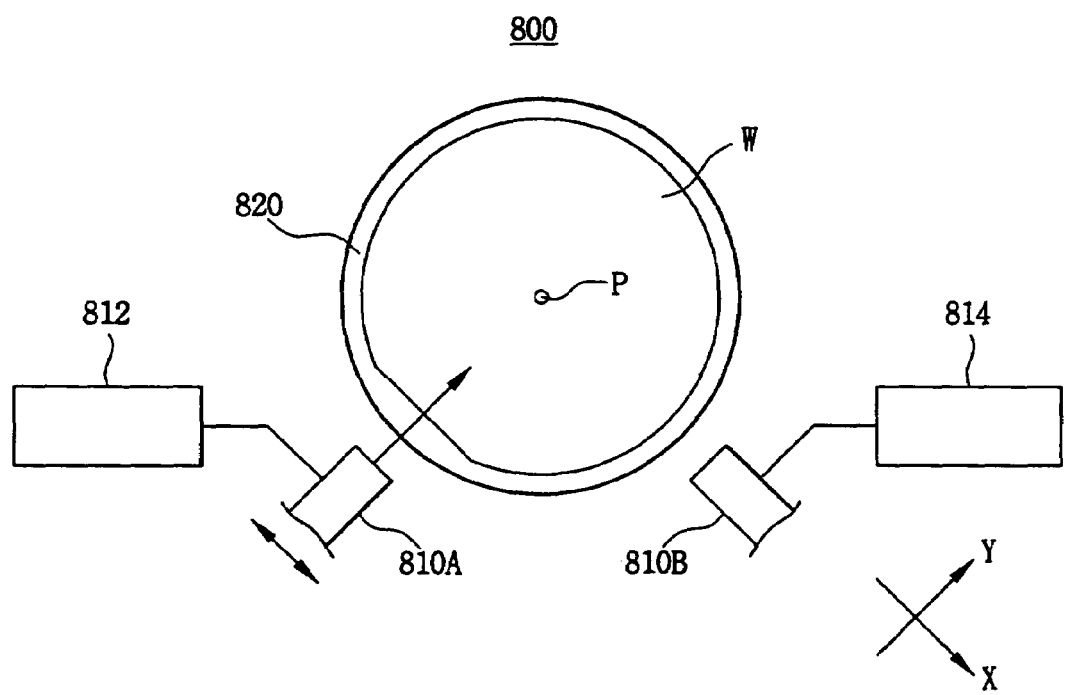
FIGS. 14B and 14C are plan views illustrating an apparatus for detecting particles on a wafer according to the eighth embodiment of the present invention.
Figure 14C:
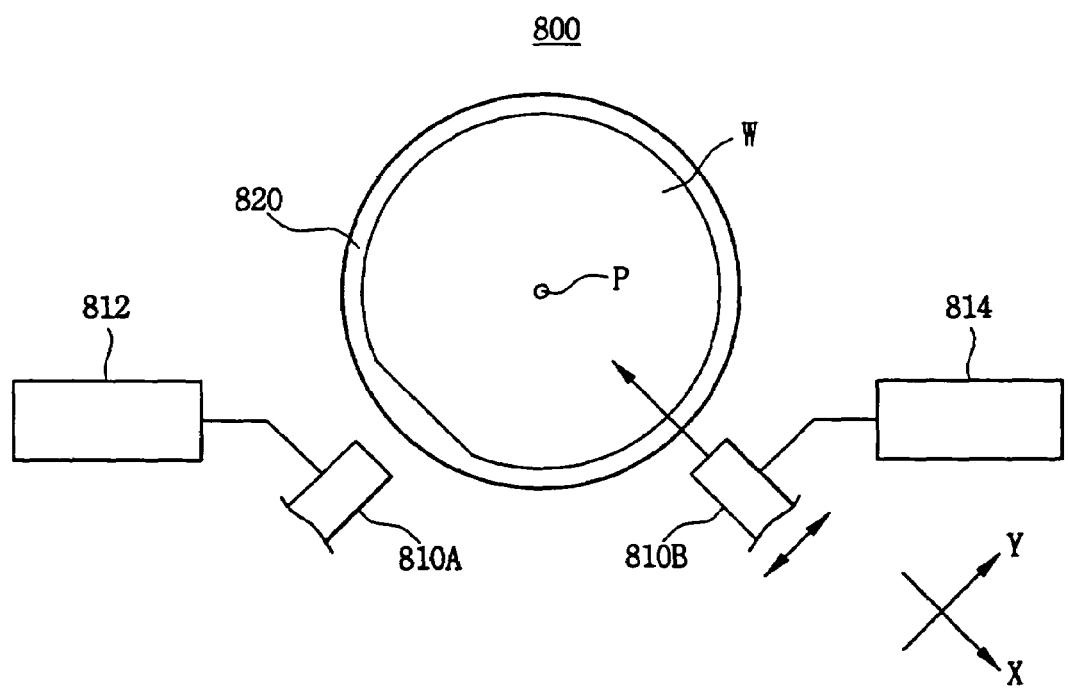

Referring to FIGS. 14B and 14C, a Y-axis is substantially perpendicular to the flat zone of the wafer W and also passes through the center of the wafer W. An X-axis is substantially perpendicular to the Y-axis and also passes through the center of the wafer W. The X-axis and the Y-axis are included in a plane that is substantially parallel to the surface of the wafer W and includes the particle P on the wafer W.

The detector 830 detects the first and second lights scattered from the particle P to recognize the actual particle P on the wafer W. The detector 830 has a dome shape to detect the first and second scattered lights.

Referring now to FIG. 14B, the first driver 812 is connected to the first emitter 810a. The first driver 812 provides a driving force to the first emitter 810a so that the first emitter 810a moves along the X-axis substantially perpendicular to the direction of the first light. Thus, the first emitter 810a linearly scans the surface of the wafer W along the X-axis.

Referring now to FIG. 14C, the second driver 814 is connected to the second emitter 810b. The second driver 814 provides a driving force to the second emitter 810b so that the second emitter 810b moves along the Y-axis substantially perpendicular to the direction of the second light. Thus, the second emitter 810b linearly scans the surface of the wafer W along the Y-axis.

Figure 15:
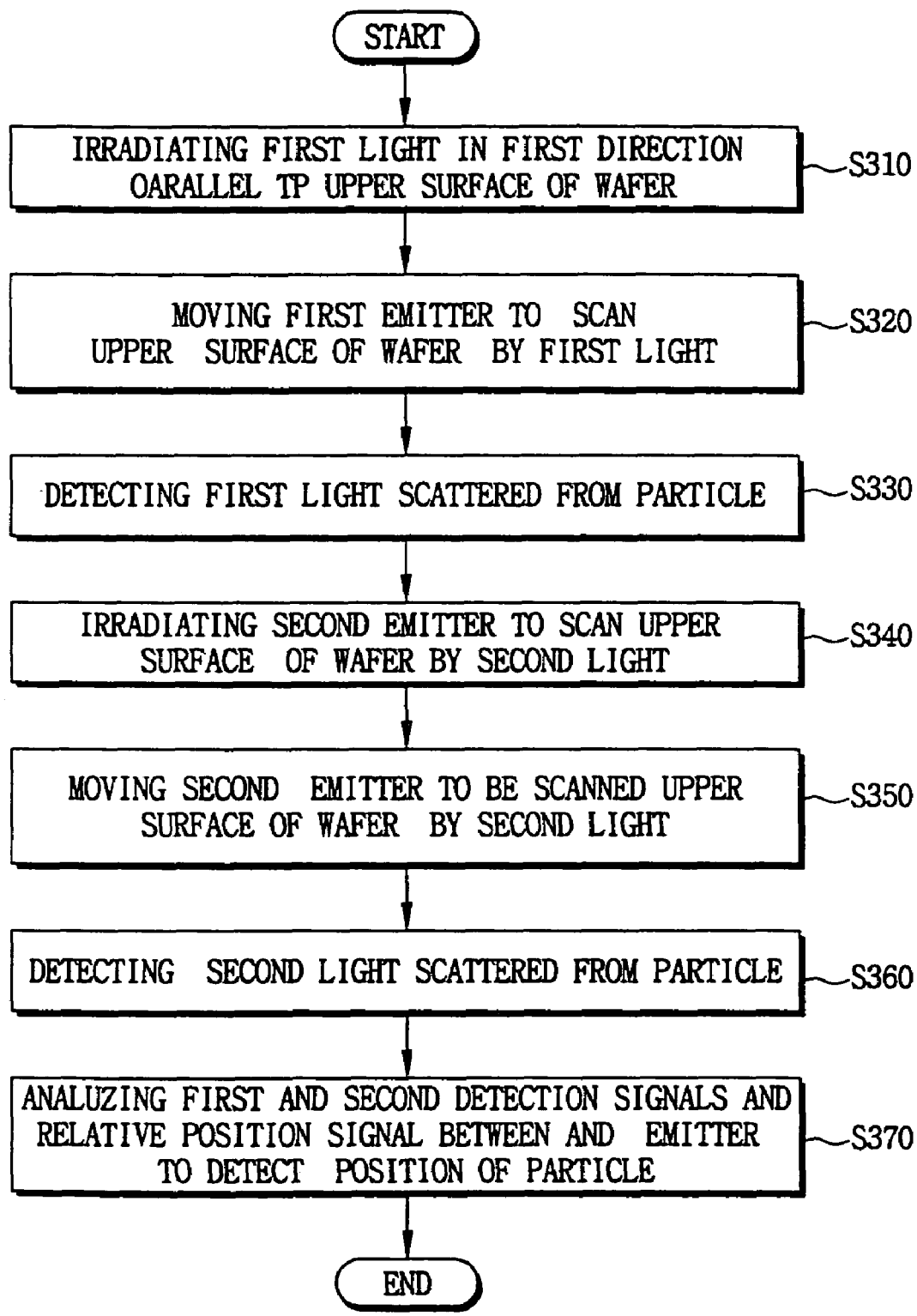
FIG. 15 is a flow chart illustrating a method for detecting particles on a wafer according to the eighth embodiment of the present invention.

Referring to FIG. 15, in step S310, a pre-aligner aligns a flat zone of the wafer W. The aligned wafer W is disposed on the stage 820. The flat zone of the wafer W is substantially perpendicular to a first direction of a first light emitted from the first emitter 810a. The first emitter 810a irradiates the first light to the particle P in the first direction substantially parallel to the Y-axis.

In step S320, the first driver 812 moves the first emitter 810a to scan the surface of the wafer W by the first emitted light along the X-axis.

In step S330, the detector 330 detects a first light scattered from the particle P.

In step S340, the second emitter 810b irradiates a second light in a second direction substantially parallel to the X-axis and the surface of the wafer W.

In step S350, the second driver 814 moves the second emitter 810b to scan the surface of the wafer W by the second emitted light along the Y-axis.

In step S360, the detector 830 detects a second light scattered from the particle P. The detector 830 generates a first detection signal corresponding to the first scattered light, a second detection signal corresponding to the second scattered light, and relative position signals between the wafer W and the first emitter 810a and between the wafer W and the second emitter 810b, respectively.

In step S370, the data processor 840 analyzes the first and second detection signals and the position signals to recognize an X and a Y coordinate of the particle P.

Figure 16A:
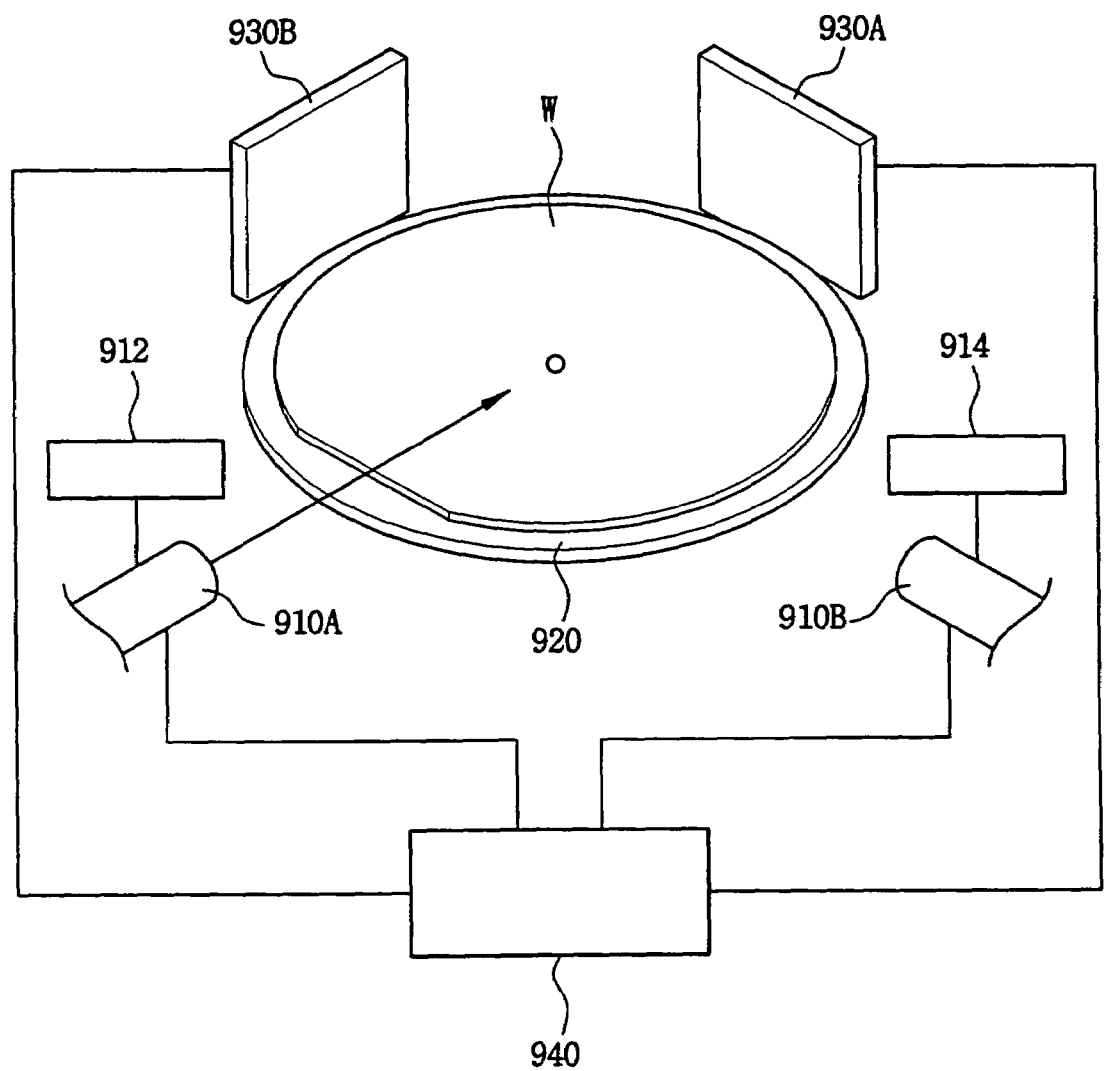
FIG. 16A is a perspective view illustrating an apparatus for detecting particles on a wafer according to a ninth embodiment of the present invention.

Referring to FIG. 16A, an apparatus 900 for detecting particles on a wafer according to the present embodiment includes a first emitter 910a for irradiating a first light to an actual particle P on a wafer W in a first direction substantially parallel to a surface of the wafer W, a second emitter 910b for irradiating a second light to the actual particle P on the wafer W in a second direction substantially parallel to the surface of the wafer W and different from the first direction, a first driver 912 for moving the first emitter 910a in a third direction substantially perpendicular to the first direction to scan the surface of the wafer W by the first light, a second driver 914 for moving the second emitter 910b in a fourth direction substantially perpendicular to the second direction to scan the surface of the wafer W by the second light, a first detector 930a for detecting the first light, a second detector 930b for detecting the second light, a data processor 940 for detecting a position of the particle P by analyzing first and second detection signals from the first and second detectors 930a and 930b and first and second position signals of the first and second emitters 910a and 910b, respectively.

Figure 16B:
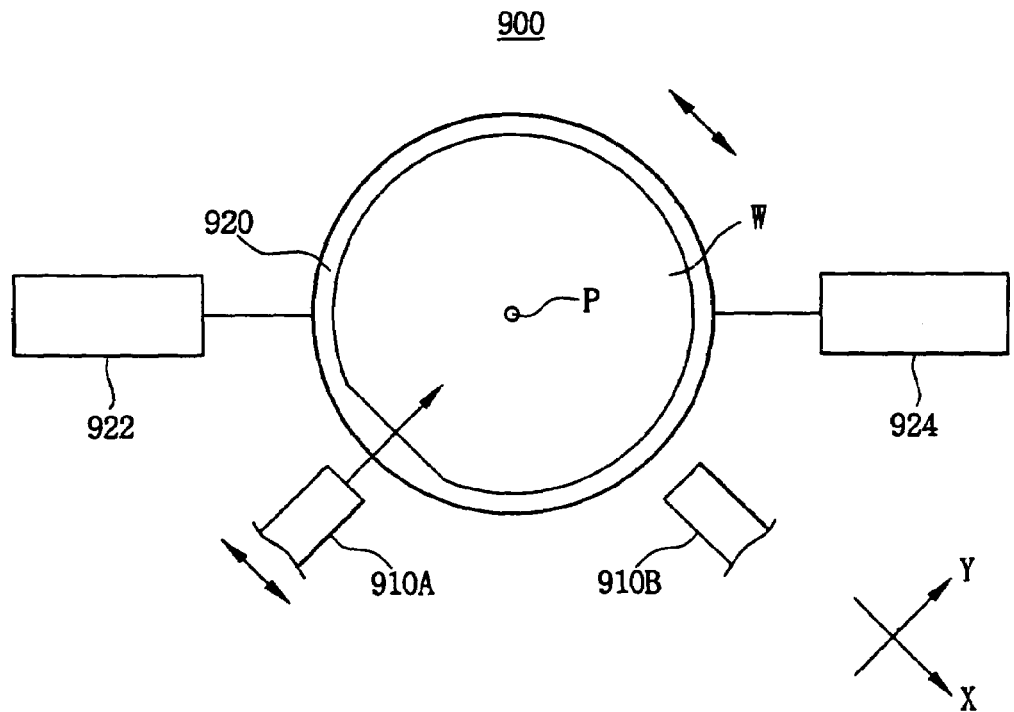
FIGS. 16B and 16C are plan views illustrating an apparatus for detecting particles on a wafer according to the ninth embodiment of the present invention.
Figure 16C:
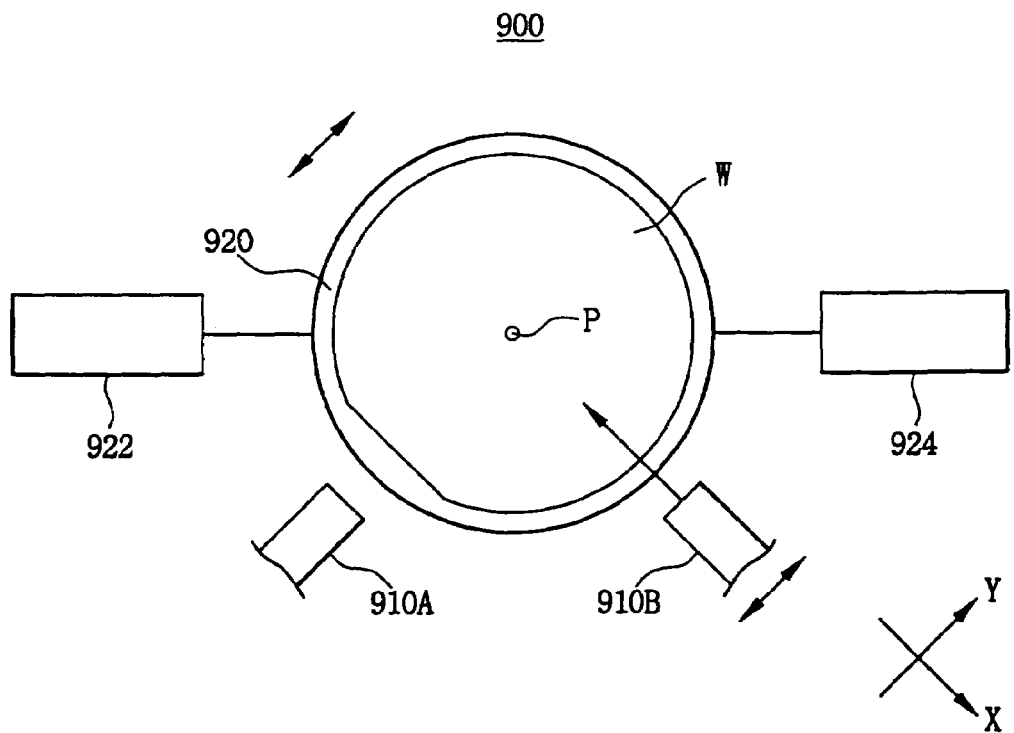

The wafer W may include a wafer upon which a pattern is not formed. Further illustrations of the wafer W are omitted. The wafer W is disposed on the stage 920. A flat zone of the wafer W is perpendicular to the directions of the first light. In FIGS. 16B and 16C, a Y-axis is substantially perpendicular to the flat zone of the wafer W and also passes through the center of the wafer W. An X-axis is substantially perpendicular to the Y-axis and also passes through the center of the wafer W. The X-axis and the Y-axis are included in a plane that is substantially parallel to the surface of the wafer W and includes the particle P on the wafer W.

The first and second detectors 930a and 930b detect the first and second lights emitted from the first and second emitters 910a and 910b to recognize the actual particle P on the wafer W. The first and second detectors 930a and 930b have a plate shape to detect the first and second emitted lights, respectively.

Referring now to FIG. 16B, the first driver 912 is connected to the first emitter 910a. The first driver 912 provides a driving force to the first emitter 910a so that the first emitter 910a moves along the X-axis substantially perpendicular to the direction of the first light. Thus, the first emitter 910a linearly scans the surface of the wafer W along the X-axis.

Referring now to FIG. 16C, the second driver 914 is connected to the second emitter 910b. The second driver 914 provides a driving force to the second emitter 910b so that the second emitter 910b moves along the Y-axis substantially perpendicular to the direction of the second light. Thus, the second emitter 910b linearly scans the surface of the wafer W along the Y-axis.

According to the invention, the apparatus detects the actual particles using the lights irradiated from the emitter in two directions. Accordingly, the apparatus according to present invention only detects the actual particles on the wafer regardless of a layer or the COP formed on the wafer.

Additionally, since the particles is recognized via double scanning in a direction substantially parallel to the surface of the wafer, the particles may be rapidly detected. Therefore, the apparatus for detecting particles may inspect a plurality of wafers for a short time.

Having described the preferred embodiments of the present invention, it is noted that modifications and variations can be made by persons skilled in the art in light of the above teachings. It is therefore to be understood that changes may be made in the particular embodiment of the present invention disclosed which is within the scope and the spirit of the invention outlined by the appended claims.

What is claimed is:

1. An apparatus for detecting particles located on an object comprising:
    an emitter for irradiating lights to the particles on the object in a direction substantially parallel to a surface of the object, the object being disposed on a stage;
    a driver for generating a relative motion between the emitter and the object for scanning the surface of the object with the lights; and
    a detector for detecting the lights emitted from the emitter or lights scattered from the particle.

2. The apparatus of claim 1, wherein the driver is in communication with the emitter to move the emitter in a second direction which is different from the direction of the emitted lights.

3. The apparatus of claim 1, wherein the driver is connected to the stage for moving the stage in a second direction which is different from the direction of the emitted lights.

4. The apparatus of claim 1, wherein the detector is located in a position which is opposite to the emitter and which is centered on the object.

5. The apparatus of claim 1, wherein the detector is disposed over the object and has a dome shape.

6. The apparatus of claim 1, wherein the object comprises a wafer.

7. An apparatus for detecting particles located on an object comprising:
    an emitter for irradiating a first light and a second light to the particles on the object being disposed on a stage in a first direction and a second direction which are substantially parallel to a surface of the object;
    a first driver for generating a relative motion between the emitter and the object for irradiating the first and second lights to the surface of the object;
    a second driver for generating a relative motion between the emitter and the object for scanning the surface of the object with the first and second lights;
    a detector for detecting the first and second lights emitted from the emitter or the first and second lights scattered from the particles, and for producing a first and second detection signals and a relative position signal between the emitter and the object; and
    a data processor for analyzing the first and second detection signals and the relative position signal between the emitter and the object from the detector to determine the position of the particles.

8. The apparatus of claim 7, further comprising a display for displaying the position of the particles.

9. The apparatus of claim 7, wherein the object comprises a wafer.

10. The apparatus of claim 7, wherein the first driver is connected to the stage to rotate the stage, and the second driver is connected to the emitter to move the emitter in a third direction different from the first direction during irradiation of the first light, and in a fourth direction different from the second direction during irradiation of the second light, respectively.

11. The apparatus of claim 7, wherein the first driver is connected to the stage to rotate the stage, and the second driver is connected to the stage to move the stage in a third direction different from the first direction during the irradiation of the first light, and in a fourth direction different from the second direction during the irradiation of the second lights, respectively.

12. The apparatus of claim 7, wherein the first driver is connected to the emitter to rotate the emitter about the object, and the second driver is connected to the emitter to move the emitter in a third direction different from the first direction during the irradiation of the first light, and in a fourth direction different from the second direction during the irradiation of the second light, respectively.

13. The apparatus of claim 12, further comprising a third driver for rotating the detector to a position centered on the object opposite to the emitter.

14. The apparatus of claim 7, wherein the first driver is connected to the emitter to rotate the emitter to a position centered on the object, and the second driver is connected to the stage to move the stage in a third direction different from the first direction during the irradiation of the first light, and in a fourth direction different from the second direction during the irradiation of the second light, respectively.

15. The apparatus of claim 7, wherein the detector is located opposite to the emitter centered on the object.

16. The apparatus of claim 15, wherein the detector has a dome shape.

17. An apparatus for detecting particles located on an object comprising:
a first emitter for irradiating a first light to the particles on the object disposed on a stage in a first direction substantially parallel to a surface of the object;
a second emitter for irradiating a second light to the particles in a second direction substantially parallel to the surface of the object;
a first driver for generating a first relative motion between the first emitter and the object to scan the surface of the object by the first light;
a second driver for generating a second relative motion between the second emitter and the object to scan the surface of the object by the second light;
a detector for detecting the first and second emitted lights or the first and second lights scattered from the particles, and for generating first and second detection signals to determine positions of the particles; and
a data processor for analyzing the first and second detection signals to determine positions of the particles, the first and second detection signals comprising a first relative position signal between the first emitter and the object and a second relative position signal between the second emitter and the object from the detector.

18. The apparatus of claim 17, wherein the first driver is connected to the first emitter to move the first emitter in a third direction different from the first direction, and the second driver is connected to the second emitter to move the second emitter in a fourth direction different from the second direction.

19. The apparatus of claim 17, wherein the first driver is connected to the stage to move the stage in a third direction different from the first direction, and the second driver is connected to the stage to move the stage in a fourth direction different from the second direction.

20. A method for detecting particles located on an object comprising:
irradiating a light from an emitter to the particles on the object in a direction substantially parallel to a surface of the object;
generating a relative motion between the emitter and the object during irradiation of the light to scan the surface of the object with the light; and
detecting the light irradiated from the emitter or the light scattered from the particles employing a dome shaped detector disposed over the object.

21. The method of claim 20, wherein the emitter moves in a second direction different from the direction of the light during an irradiation of the light.

22. The method of claim 20, wherein the object moves in a second direction different from the direction of the light during the irradiation of the light.

23. A method for detecting particles located on an object comprising:
irradiating a first light from an emitter to the particles on the object in a first direction substantially parallel to a surface of the object;
generating a first relative motion between the emitter and the object during irradiation of the first light to scan the surface of the object with the first light;
detecting the first light irradiated from the emitter or a first light scattered from the particle;
generating a relative motion between the emitter and the object;
irradiating a second light from the emitter to the particles in a second direction that is different from the first direction and is parallel to the surface of the object;
generating a second relative motion between the emitter and the object during irradiation of the second light to scan the surface of the object with the second light;
detecting the second light irradiated from the emitter or a second light scattered from the particles; and
analyzing first and second detection signals and a relative position signal between the emitter and the object created from detecting the first and second lights to recognize a position of the particles.

24. The method of claim 23, further comprising displaying the positions of the particles.

25. The method of claim 23, wherein generating the first relative motion further comprises moving the emitter relative to the object in a third direction different from the first direction during an irradiation of the first light, generating the relative rotary motion includes rotating the object, and generating the second relative motion includes moving the emitter relative to the object in a fourth direction different from the second direction during irradiation of the second light.

26. The method of claim 23, wherein generating the first relative motion further comprises moving the object relative to the emitter in a third direction different from the first direction during the irradiation of the first light, generating the relative rotary motion includes rotating the object, and generating the second relative motion includes moving the object relative to the emitter in a fourth direction different from the second direction during the irradiation of the second light.

27. The method of claim 23, wherein generating the first relative motion further comprises moving the emitter relative to the object in a third direction different from the first direction during the irradiation of the first light, generating the relative rotary motion includes rotating the emitter about the object, and generating the second relative motion includes moving the emitter relative to the object in a fourth direction different from the second direction during the irradiation of the second light.

28. The method of claim 23, wherein generating the first relative motion further comprises moving the object relative to the emitter in a third direction different from the first direction during the irradiation of the first light, generating the relative rotary motion includes rotating the emitter about the object, and generating the second relative motion includes moving the object relative to the emitter in a fourth direction different from the second direction during the irradiation of the second light.

29. A method for detecting particles on an object comprising:
   irradiating a first light from a first emitter to particles on the object in a first direction substantially parallel to a surface of the object;
   generating a first relative motion between the first emitter and the object in a third direction different from the first direction during irradiation of the first light to scan the surface of the object by the first light;
   detecting the first light irradiated from the emitter or a first light scattered from the particles;
   irradiating a second light from a second emitter to the particle in a second direction that is different from the first direction and is substantially parallel to the surface of the object;
   generating a second relative motion between the second emitter and the object in a fourth direction different from the second direction during irradiation of the second light to scan the surface of the object by the second light;
   detecting the second light irradiated from the emitter or a second light scattered from the particles; and
   analyzing first and second detection signals to determine the positions of the particles, the first and second detection signals comprising a relative position signal between the emitter and the object created from detecting the first and second lights.

30. The method of claim 29, wherein generating the first relative motion further comprises moving the first emitter relative to the object generating the relative rotary motion includes rotating the object and generating the second relative motion further comprises moving the second emitter relative to the object.

31. The method of claim 29, wherein generating the first relative motion further comprises moving the object relative to the first emitter, and generating the second relative motion further comprises moving the object relative to the second emitter.

32. An apparatus for detecting particles located on an object comprising:
   an emitter for irradiating lights to the particles, the object being disposed on a stage in a direction substantially parallel to a surface of the object;
   a driver for generating a relative motion between the emitter and the object for scanning the surface of the object with the lights; and
   a detector for detecting the lights emitted from the emitter or lights scattered from the particle, wherein the detector is disposed over the object and has a dome shape.

33. An apparatus for detecting particles located on an object comprising:
   an emitter for irradiating a first light and a second light to the particles, the object being disposed on a stage in a first direction and a second direction which are substantially parallel to a surface of the object;
   a first driver for generating a relative motion between the emitter and the object for irradiating the first and second lights to the surface of the object;
   a second driver for generating a relative motion between the emitter and the object for scanning the surface of the object with the first and second lights;
   a detector for detecting the first and second lights emitted from the emitter or the first and second lights scattered from the particles, and for producing a first and second detection signals and a relative position signal between the emitter and the object; and
   a data processor for analyzing the first and second detection signals and the relative position signal between the emitter and the object from the detector to determine the position of the particles,
   wherein the first driver is connected to the stage to rotate the stage, and the second driver is connected to the emitter to move the emitter in a third direction different from the first direction during irradiation of the first light, and in a fourth direction different from the second direction during irradiation of the second light, respectively.

34. An apparatus for detecting particles located on an object comprising:
   an emitter for irradiating a first light and a second light to the particles, the object being disposed on a stage in a first direction and a second direction which are substantially parallel to a surface of the object;
   a first driver for generating a relative motion between the emitter and the object for irradiating the first and second lights to the surface of the object;
   a second driver for generating a relative motion between the emitter and the object for scanning the surface of the object with the first and second lights;
   a detector for detecting the first and second lights emitted from the emitter or the first and second lights scattered from the particles, and for producing a first and second detection signals and a relative position signal between the emitter and the object; and
   a data processor for analyzing the first and second detection signals and the relative position signal between the emitter and the object from the detector to determine the position of the particles,
   wherein the first driver is connected to the stage to rotate the stage, and the second driver is connected to the stage to move the stage in a third direction different from the first direction during the irradiation of the first light, and in a fourth direction different from the second direction during the irradiation of the second lights, respectively.

35. An apparatus for detecting particles located on an object comprising:
   an emitter for irradiating a first light and a second light to the particles, the object being disposed on a stage in a first direction and a second direction which are substantially parallel to a surface of the object;
   a first driver for generating a relative motion between the emitter and the object for irradiating the first and second lights to the surface of the object;
   a second driver for generating a relative motion between the emitter and the object for scanning the surface of the object with the first and second lights;
   a detector for detecting the first and second lights emitted from the emitter or the first and second lights scattered from the particles, and for producing a first and second detection signals and a relative position signal between the emitter and the object; and a data processor for analyzing the first and second detection signals and the relative position signal between the emitter and the object from the detector to determine the position of the particles, wherein the first driver is connected to the emitter to rotate the emitter about the object, and the second driver is connected to the emitter to move the emitter in a third direction different from the first direction during the irradiation of the first light, and in a fourth direction different from the second direction during the irradiation of the second light, respectively.

36. An apparatus for detecting particles located on an object comprising:

an emitter for irradiating a first light and a second light to the particles, the object being disposed on a stage in a first direction and a second direction which are substantially parallel to a surface of the object;

a first driver for generating a relative motion between the emitter and the object for irradiating the first and second lights to the surface of the object;

a second driver for generating a relative motion between the emitter and the object for scanning the surface of the object with the first and second lights;

a third driver for rotating the detector to a position centered on the object opposite to the emitter;

a detector for detecting the first and second lights emitted from the emitter or the first and second lights scattered from the particles, and for producing a first and second detection signals and a relative position signal between the emitter and the object; and a data processor for analyzing the first and second detection signals and the relative position signal between the emitter and the object from the detector to determine the position of the particles.

37. An apparatus for detecting particles located on an object comprising:

an emitter for irradiating a first light and a second light to the particles, the object being disposed on a stage in a first direction and a second direction which are substantially parallel to a surface of the object;

a first driver for generating a relative motion between the emitter and the object for irradiating the first and second lights to the surface of the object;

a second driver for generating a relative motion between the emitter and the object for scanning the surface of the object with the first and second lights;

a detector for detecting the first and second lights emitted from the emitter or the first and second lights scattered from the particles, and for producing a first and second detection signals and a relative position signal between the emitter and the object; and a data processor for analyzing the first and second detection signals and the relative position signal between the emitter and the object from the detector to determine the position of the particles, wherein the first driver is connected to the emitter to rotate the emitter to a position centered on the object, and the second driver is connected to the stage to move the stage in a third direction different from the first direction during the irradiation of the first light, and in a fourth direction different from the second direction during the irradiation of the second light, respectively.

38. An apparatus for detecting particles located on an object comprising:

an emitter for irradiating a first light and a second light to the particles, the object being disposed on a stage in a first direction and a second direction which are substantially parallel to a surface of the object;

a first driver for generating a relative motion between the emitter and the object for irradiating the first and second lights to the surface of the object;

a second driver for generating a relative motion between the emitter and the object for scanning the surface of the object with the first and second lights;

a dome shaped detector for detecting the first and second lights emitted from the emitter or the first and second lights scattered from the particles, and for producing a first and second detection signals and a relative position signal between the emitter and the object; and a data processor for analyzing the first and second detection signals and the relative position signal between the emitter and the object from the detector to determine the position of the particles.

* * * * *